(12) United States Patent
Deng et al.

(10) Patent No.: US 8,946,216 B2
(45) Date of Patent: Feb. 3, 2015

(54) INDAZOLE DERIVATIVES USEFUL AS ERK INHIBITORS

(75) Inventors: Yonqi Deng, Newton, MA (US); Gerald W. Shipps, Jr., Stoneham, MA (US); Sie-Mun Lo, Springfield, VA (US); Liang Zhu, Waltham, MA (US); Alan B. Cooper, West Caldwell, NJ (US); Kiran Muppalla, Cranford, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/819,366

(22) PCT Filed: Aug. 29, 2011

(86) PCT No.: PCT/US2011/049483
§ 371 (c)(1),
(2), (4) Date: Feb. 27, 2013

(87) PCT Pub. No.: WO2012/030685
PCT Pub. Date: Mar. 8, 2012

(65) Prior Publication Data
US 2013/0158020 A1    Jun. 20, 2013

Related U.S. Application Data

(60) Provisional application No. 61/379,176, filed on Sep. 1, 2010.

(51) Int. Cl.
| | |
|---|---|
| C07D 401/14 | (2006.01) |
| C07D 413/14 | (2006.01) |
| C07D 417/14 | (2006.01) |
| A61K 31/541 | (2006.01) |
| A61K 31/5377 | (2006.01) |
| A61K 31/496 | (2006.01) |
| A61K 31/4545 | (2006.01) |
| A61K 45/06 | (2006.01) |
| C07D 417/12 | (2006.01) |
| C07D 491/113 | (2006.01) |

(52) U.S. Cl.
CPC .............. *A61K 31/541* (2013.01); *A61K 45/06* (2013.01); *C07D 401/14* (2013.01); *C07D 413/14* (2013.01); *C07D 417/12* (2013.01); *C07D 417/14* (2013.01); *C07D 491/113* (2013.01); *A61K 31/4545* (2013.01); *A61K 31/496* (2013.01); *A61K 31/5377* (2013.01)
USPC .......................... 514/234.5; 544/131; 544/140

(58) Field of Classification Search
USPC ................................ 544/131, 140; 514/234.5
See application file for complete search history.

(56) References Cited

U.S. PATENT DOCUMENTS

2009/0203691 A1    8/2009    Oinuma et al.

FOREIGN PATENT DOCUMENTS

| WO | 2007070398 A1 | 6/2007 |
| WO | 2008153858 A1 | 12/2008 |
| WO | 2011041152 A1 | 4/2011 |

OTHER PUBLICATIONS

Burkhard, K. et al, Development of Extracellular Signal-Regulated Kinase Inhibitor, Curr Top Med Chem., 2009, 678-689, 9-8.

*Primary Examiner* — Kahsay Habte
(74) *Attorney, Agent, or Firm* — Richard S. Parr; Laura M. Ginkel

(57) ABSTRACT

The present invention provides a compound of the Formula I: Formula I or a pharmaceutically acceptable salt, solvate or ester thereof, wherein R, R1, R2, R3, R4, X, m and n are as defined herein. The compounds are ERK inhibitors. Also disclosed are pharmaceutical compositions comprising the above compounds and methods of treating cancer using the same.

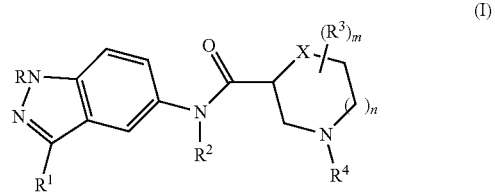

13 Claims, No Drawings

INDAZOLE DERIVATIVES USEFUL AS ERK INHIBITORS

REFERENCE TO RELATED APPLICATION

This application claims the benefit of U.S. Provisional Application No. 61/379,176 filed on Sep. 1, 2010.

FIELD OF THE INVENTION

This invention related to compounds which can act as inhibitors of kinases, such as ERK, to uses of such compounds and to their preparation

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumors. Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thryroid cancer, colorectal cancer, lung cancer, breast cancer, and ovarian cancer. Such a contribution is provided by this invention.

PCT publications WO 2007/070398 A1 and WO 2008/153858 A1 disclose polycyclic indazole derivatives useful as ERK inhibitors for the treatment of cancer.

SUMMARY OF THE INVENTION

In its many embodiments, the present invention provides a novel class of compounds, pharmaceutical compositions comprising one or more said compounds, and methods for using said compounds for treating or preventing a disease associated with one or more kinases such as ERK1 and ERK2.

Accordingly, in one aspect, the present invention provides a compound of the Formula I:

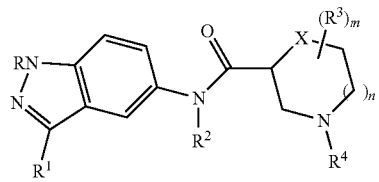

Formula I or a pharmaceutically acceptable salt, solvate or ester thereof, wherein:

R is H;
$R^1$ is selected from the group consisting of aryl, heterocyclyl and —C(=O)—$NR^5R^6$;
$R^2$ is H or alkyl;
X is selected from the group consisting of —$NR^7$, —C($R^8$)($R^9$)—, —O—, —S—, —S(=O)—, and —S(=O)$_2$;
each $R^3$ independently is selected from the group consisting of alkyl, aryl, hydroxyl, and —S-alkyl, or wherein two $R^3$ groups together with the same carbon atom to which both are attached form —C(=O)—;
m is 0, 1, or 2;
n is 0 or 1;
$R^4$ is selected from the group consisting of H, alkyl, aryl, —C(=O)-aryl, and —C(=O)—O-alkyl;
$R^5$, $R^6$, and $R^7$ independently are H or alkyl;
$R^8$ and $R^9$ independently are H, alkyl or aryl; or —C($R^8$)($R^9$)— together is heterocyclyl.

In another aspect, the compounds of Formula I, or the pharmaceutically acceptable salts, solvates, or esters thereof can be useful as protein kinase inhibitors.

In another aspect, the compounds of Formula I, or the pharmaceutically acceptable salts, solvates, or esters thereof are useful as protein kinase inhibitors that inhibit the activity of ERK1 and/or the activity of ERK2.

In another aspect, the compounds of Formula I, or the pharmaceutically acceptable salts, solvates, or esters thereof are useful as inhibitors of the phosphorylation of ERK1 and ERK2.

In another aspect, the present invention provides a pharmaceutical composition comprising at least one compound of Formula I, or a pharmaceutically acceptable salt, solvate, or ester thereof and a pharmaceutically acceptable carrier.

In another aspect, the present invention also provides a method of treating cancer in a patient in need of such treatment, said method comprising administering an effective amount of at least one compound of Formula I, or a pharmaceutically acceptable salt, solvate, or ester thereof.

DETAILED DESCRIPTION OF THE INVENTION

As used above, and throughout this disclosure, the following terms, unless otherwise indicated, shall be understood to have the following meanings:

"Patient" includes both human and animals.

"Mammal" means humans and other mammalian animals.

"At least one", as used in reference to the number of compounds of this invention means for example 1-6, generally 1-4, more generally 1, 2 or 3, and usually one or two, and more usually one;

"At least one", as used in reference to the number of chemotherapeutic agents used, means for example 1-6, generally 1-4, more generally 1, 2 or 3, and usually one or two, or one;

"At least one", or "substituted with a (followed by a named substituent)" as used in reference to the number of substituents attached to a particular group, such as an alkyl group, a cycloalkyl group, a heterocyclyl group, an aryl group and an heteroaryl group, means for example 1-6, generally 1-4, more generally 1, 2 or 3, and usually one or two, or one;

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. In one embodiment, the alkyl group contains 1 to 3 carbon atoms, i.e., $C_1$-$C_3$ alkyl. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, heterocyclyl, heteroaryl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, heterocyclyl, heteroaryl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, hydroxyl, hydroxyalkyl, alkoxy, aryloxy, acyl, aroyl, halo, nitro, cyano, carboxy, alkoxycarbonyl, aryloxycarbonyl, alkylsulfonyl, arylsulfonyl, heteroarylsulfonyl, alkylthio, arylthio, heteroarylthio, cycloalkyl, heterocyclyl, —C(=N—CN)—NH$_2$, —C(=NH)—NH$_2$, —C(=NH)—NH(alkyl), $Y_1Y_2N$—, $Y_1Y_2N$-alkyl-, $Y_1Y_2NC(O)$—, $Y_1Y_2NSO_2$— and —SO$_2$NY$_1$Y$_2$, wherein Y$_1$ and Y$_2$ can be the same or different and are independently selected from the group consisting of hydrogen, alkyl, aryl, cycloalkyl, heterocyclyl and heteroaryl. "Ring system substituent" may also mean a single moiety which simultaneously replaces two available hydrogens on two adjacent carbon atoms (one H on each carbon) on a ring system to form a carbocyclic or heterocyclic (aromatic or nonaromatic) ring. Examples of such moiety are methylene dioxy, ethylenedioxy, —C(CH₃)₂— and the like which form moieties such as, for example:

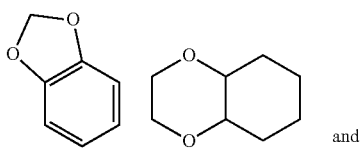 and 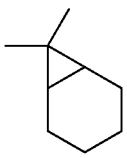.

"Heterocyclyl" means a non-aromatic saturated monocyclic or multicyclic ring system comprising about 3 to about 10 ring atoms, preferably about 5 to about 10 ring atoms, in which one or more (such as two, three, or four) of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

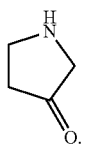

"Heterocyclenyl" means a non-aromatic monocyclic or multicyclic ring system comprising about 3 to about 10 ring atoms, preferably about 5 to about 10 ring atoms, in which one or more (e.g, two, three, or four) of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or Chia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydro-pyridinyl, 1,4-dihydropyridinyl, 1,2,3,6-tetrahydropyridinyl, 1,4,5,6-tetrahydroppimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

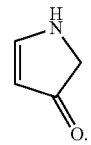

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

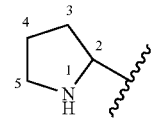

there is no —OH attached directly to carbons marked 2 and 5.

It should also be noted that tautomeric forms such as, for example, the moieties:

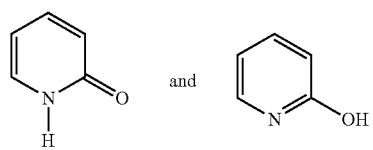 [SMILES: O=c1cccc[nH]1 ; "and" ; Oc1ccccn1]

are considered equivalent in certain embodiments of this invention.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocyclyl, $R^2$, etc.) occurs more than one time in any constituent or in Formula (1), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I), or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I, or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxyearbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of any one of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)

$Y^3$ wherein $Y^2$ is $(C_1$-$C_4)$ alkyl and $Y^3$ is $(C_1$-$C_6)$alkyl, carboxy $(C_1$-$C_6)$alkyl, amino$(C_1$-$C_4)$alkyl or mono-N— or di-N, N—$(C_1$-$C_6)$alkylaminoalkyl, —C$(Y^4)Y^5$ wherein $Y^4$ is H or methyl and $Y^5$ is mono-N— or di-N,N—$(C_1$-$C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

Pharmaceutically acceptable (i.e., non-toxic, physiologically acceptable) salts are preferred, although other salts are also useful. Salts of the compounds of Formulae I may be formed, for example, by reacting a compound of Formula I, with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCM; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

Compounds of Formula I, and salts, solvates, esters and prodrugs thereof, may exist in their tautomeric fowl (for example, as an amide or imino ether). All such tautomeric forms are contemplated herein as part of the present invention.

The compounds of Formula I as set forth herein may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of Formula I can generally be prepared by following procedures analogous to those disclosed in the Schemes and/or in the Examples hereinbelow, by substituting an appropriate isotopically labeled reagent for a non-isotopically labeled reagent.

Polymorphic forms of the compounds of Formula I, and of the salts, solvates, esters and prodrugs of the compounds of Formula I, are intended to be included in the present invention.

The following abbreviations are used below and have the following meanings:

Boc is tert-butoxycarbonyl, dba is dibenzylideneacetone, DMF is N,N-dimethylformamide, DMSO is dimethylsulfoxide, EtOAc is ethyl acetate, LCMS is liquid chromatography mass spectrometry, MeOH is methanol, NMR is nuclear magnetic resonance, PBS is phosphate buffered saline, SPA is scintillation proximity assay, Tf is triflate, TFA is trifluoroacetic acid and Xantphos is 9,9-Dimethyl-4,5-bis(diphenylphosphino)xanthene. Me4Si is tetramethyl silane, DIEA is di isopropyl ethylamine,SGC is silicagel column, TMSCHN2 is trimethylsilyl diazomethane, BBr3 is tribromoborane,m-CPBA is m-chloro perbenzoic acid, CDT is carbodiimidazole,HATU is 2-(1H-azabenzotriazol-1-yl-1,13,3-tetramethyl uranium hexafluorophosphate, NaH is sodium hydride,SiO2 is silica,CBZ is benzyloxy carbonyl, Tos is p-toluene sulfonyl,$CH_3CN$ is acetonitrile.

In another embodiment, in Formula I, $R^1$ is heterocyclyl which is pyridyl.

In another embodiment, in Formula I, $R^1$ is 3-pyridyl or 4-pyridyl.

In another embodiment, in Formula I, $R^1$ is —C(=O)—$NR^5R^6$ wherein $R^5$ is H and $R^6$ is alkyl.

In another embodiment, in Formula I, $R^1$ is —C(=O)—$NR^5R^6$ wherein $R^5$ is H and $R^6$ is alkyl, which is unsubstituted or substituted with an aryl substituent.

In another embodiment, in Formula I, $R^1$ is selected from the group consisting of —C(=O)—$NHCH_3$, —C(=O)—$NH(CH_2)_3CH_3$ and —C(=O)—$NHCH_2$-phenyl.

In another embodiment, in Formula I, $R^2$ is H.

In another embodiment, in Formula I, m is 0, i.e., Formula I becomes formula I-A:

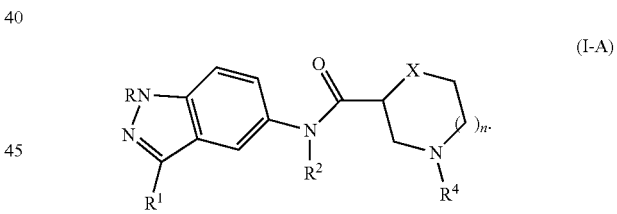

(I-A)

In another embodiment, in Formula I, m is 1, i.e., Formula I becomes Formula I-B:

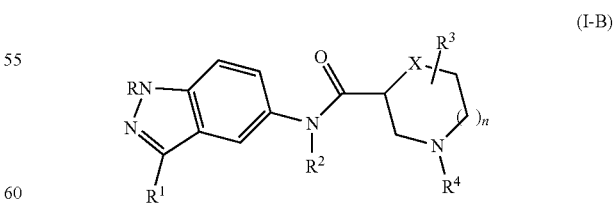

(I-B)

and $R^3$ is selected from the group consisting of hydroxyl, —S-alkyl, phenyl, and hydroxymethyl.

In another embodiment, in Formula I, m is 2, and the two $R^3$ groups together with the carbon atom to which both are attached form —C(=O)—.

In another embodiment, in Formula I,

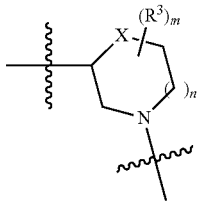

is selected from the group consisting of:

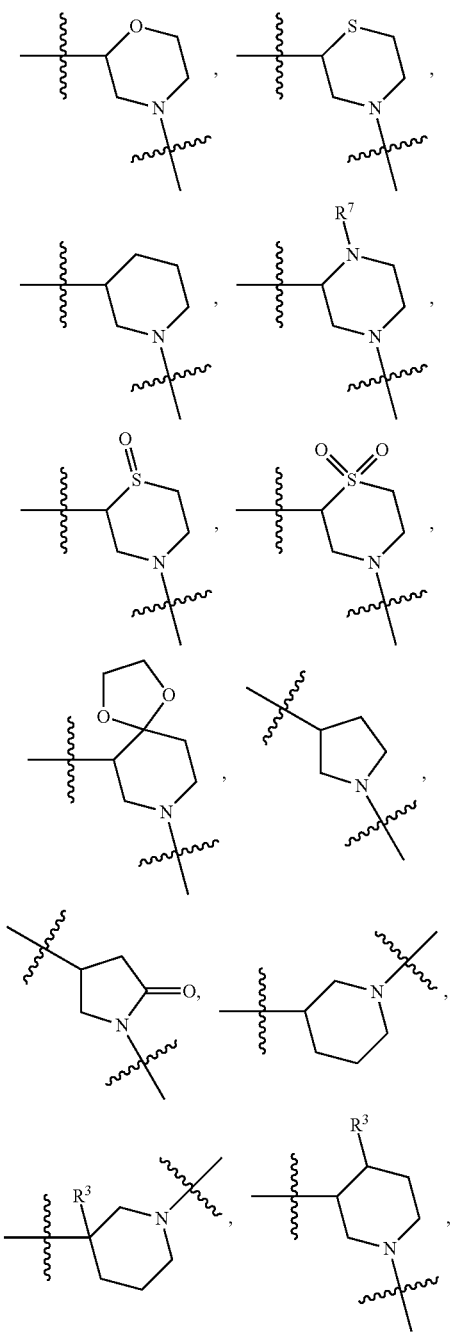

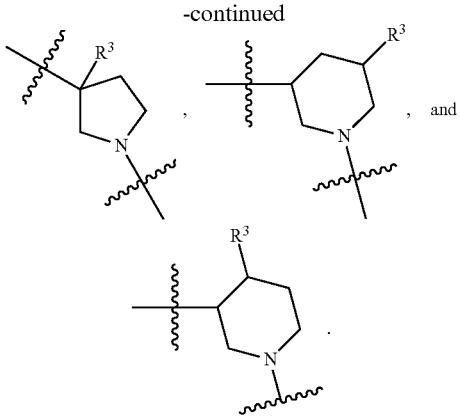

In another embodiment, in Formula I, $R^4$ is alkyl, which is unsubstituted or substituted with at least one substituent selected from the group consisting of aryl and heteroaryl.

In another embodiment, in Formula I, $R^4$ is alkyl which is substituted with a phenyl.

In another embodiment, in Formula I, $R^4$ is a $C_1$-$C_3$ alkyl which is substituted with a phenyl.

In another embodiment, in Formula I, $R^4$ is a $C_1$-$C_3$ alkyl which is substituted with a phenyl, wherein said $C_1$-$C_3$ alkyl is selected from the group consisting of —$CH_2$—, —CH($CH_3$)—, and —($CH_2$)$_3$—.

In another embodiment, in Formula I, $R^4$ is alkyl which is substituted with a phenyl, wherein said phenyl is unsubstituted or substituted with at least one substituent selected from the group consisting of halo, haloalkyl, alkoxy, cyano, —N(alkyl)$_2$, —S-alkyl, and —S(=O)$_2$-alkyl.

In another embodiment, in Formula I, $R^4$ is alkyl which is substituted with a heteroaryl selected from the group consisting of pyridyl, thiazolyl, and thiophenyl.

In another embodiment, in Formula I, $R^4$ is alkyl which is substituted with a heteroaryl is —$CH_2$—.

In another embodiment, the compound of Formula I is selected from the group consisting of:

N-[3-[6-(1-METHYLETHOXY)-3-PYRIDINYL]-1H-INDAZOL-5-YL]-4-(PHENYLMETHYL)-2-MORPHOLINECARBOXAMIDE;

N-[3-[6-(1-METHYLETHOXY)-3-PYRIDINYL]-1H-INDAZOL-5-YL]-2-MORPHOLINECARBOXAMIDE;

N-[3-(4-PYRIDINYL)-1H-INDAZOL-5-YL]-4-(4-THIAZOLYLMETHYL)-2-MORPHOLINECARBOXAMIDE;

N-[3-(4-PYRIDINYL)-1H-INDAZOL-5-YL]-4-(3-THIENYLMETHYL)-2-MORPHOLINECARBOXAMIDE;

4-[(2-FLUOROPHENYL)METHYL]-N-[3-(4-PYRIDINYL)-1H-INDAZOL-5-YL]-2-MORPHOLINECARBOXAMIDE;

N-[3-(4-PYRIDINYL)-1H-INDAZOL-5-YL]-4-(2-PYRIDINYLMETHYL)-2-MORPHOLINECARBOXAMIDE;

N-[3-(4-PYRIDINYL)-1H-INDAZOL-5-YL]-4-(2-PYRIDINYLMETHYL)-2-MORPHOLINECARBOXAMIDE;

4-[(2-BROMOPHENYL)METHYL]-N-[3-(4-PYRIDINYL)-1H-INDAZOL-5-YL]-2-THIOMORPHOLINECARBOXAMIDE;

4-[(2-BROMOPHENYL)METHYL]-N-[3-(4-PYRIDINYL)-1H-INDAZOL-5-YL]-2-MORPHOLINECARBOXAMIDE;

N-[3-(4-PYRIDINYL)-1H-INDAZOL-5-YL]-4-(3-PYRIDINYLMETHYL)-2-THIOMORPHOLINECARBOXAMIDE;

4-[(2-CHLOROPHENYL)METHYL]-N-[3-(4-PYRIDI-NYL)-1H-INDAZOL-5-YL]-2-THIOMORPHOLIN-ECARBOXAMIDE;
4-[(2-FLUOROPHENYL)METHYL]-N-[3-(4-PYRIDI-NYL)-1H-INDAZOL-5-YL]-2-THIOMORPHOLIN-ECARBOXAMIDE;
4-[(2-METHYL-4-THIAZOLYL)METHYL]-N-[3-(4-PY-RIDINYL)-1H-INDAZOL-5-YL]-2-THIOMORPHOLI-NECARBOXAMIDE;
N-[3-(4-PYRIDINYL)-1H-INDAZOL-5-YL]-4-(2-PY-RIDINYLMETHYL)-2-THIOMORPHOLINECAR-BOXAMIDE;
4-(4-FLUOROPHENYL)-N-[3-(4-PYRIDINYL)-1H-IN-DAZOL-5-YL]-3-PIPERIDINECARBOXAMIDE;
N-[3-(4-PYRIDINYL)-1H-INDAZOL-5-YL]-4-(4-THIAZ-OLYLMETHYL)-2-THIOMORPHOLINECARBOXA-MIDE;
N-[3-(4-PYRIDINYL)-1H-INDAZOL-5-YL]-4-(3-THIE-NYLMETHYL)-2-THIOMORPHOLINECARBOXAM-IDE;
4-[(2-CHLOROPHENYL)METHYL]-N-[3-(4-PYRIDI-NYL)-1H-INDAZOL-5-YL]-2-MORPHOLINECAR-BOXAMIDE;
N-[3-(4-PYRIDINYL)-1H-INDAZOL-5-YL]-2-MOR-PHOLINECARBOXAMIDE;
N-[3-(4-PYRIDINYL)-1H-INDAZOL-5-YL]-2-THIO-MORPHOLINECARBOXAMIDE;
PHENYLMETHYL 3-[[[3-(4-PYRIDINYL)-1H-INDA-ZOL-5-YL]AMINO]CARBONYL]-1-PIPERAZIN-ECARBOXYLATE;
4-[(2-METHYL-4-THIAZOLYL)METHYL]-N-[3-(4-PY-RIDINYL)-1H-INDAZOL-5-YL]-2-MORPHOLIN-ECARBOXAMIDE;
N-[3-(4-PYRIDINYL)-1H-INDAZOL-5-YL]-4-(3-PY-RIDINYLMETHYL)-2-MORPHOLINECARBOXAM-IDE;
4-(PHENYLMETHYL)-N-[3-(4-PYRIDINYL)-1H-INDA-ZOL-5-YL]-2-MORPHOLINECARBOXAMIDE;
1-[(2-BROMOPHENYL)METHYL]-N-[3-(4-PYRIDI-NYL)-1H-INDAZOL-5-YL]-3-PIPERIDINECAR-BOXAMIDE;
1-[(2-FLUOROPHENYL)METHYL]-N-[3-(4-PYRIDI-NYL)-1H-INDAZOL-5-YL]-3-PIPERIDINECAR-BOXAMIDE;
1-[(2-CHLOROPHENYL)METHYL]-N-[3-(4-PYRIDI-NYL)-1H-INDAZOL-5-YL]-3-PIPERIDINECAR-BOXAMIDE;
1-(PHENYLMETHYL)-N-[3-(4-PYRIDINYL)-1H-INDA-ZOL-5-YL]-3-PIPERIDINECARBOXAMIDE;
N-[3-(4-PYRIDINYL)-1H-INDAZOL-5-YL]-3-PIPERIDI-NECARBOXAMIDE;
1-METHYL-N-[3-(4-PYRIDINYL)-1H-INDAZOL-5-YL]-3-PIPERIDINECARBOXAMIDE;
4-[(4-CHLOROPHENYL)METHYL]-N-[3-(4-PYRIDI-NYL)-1H-INDAZOL-5-YL]-2-MORPHOLINECAR-BOXAMIDE;
4-[(3-METHOXYPHENYL)METHYL]-N-[3-(4-PYRIDI-NYL)-1H-INDAZOL-5-YL]-2-MORPHOLINECAR-BOXAMIDE;
4-[(3-CHLOROPHENYL)METHYL]-N-[3-(4-PYRIDI-NYL)-1H-INDAZOL-5-YL]-2-MORPHOLINECAR-BOXAMIDE;
4-[(4-CYANOPHENYL)METHYL]-N-[3-(4-PYRIDI-NYL)-1H-INDAZOL-5-YL]-2-MORPHOLINECAR-BOXAMIDE;
4-[(3-CYANOPHENYL)METHYL]-N-[3-(4-PYRIDI-NYL)-1H-INDAZOL-5-YL]-2-MORPHOLINECAR-BOXAMIDE;
4-[(2-CYANOPHENYL)METHYL]-N-[3-(4-PYRIDI-NYL)-1H-INDAZOL-5-YL]-2-MORPHOLINECAR-BOXAMIDE;
4-[(4-METHOXYPHENYL)METHYL]-N-[3-(4-PYRIDI-NYL)-1H-INDAZOL-5-YL]-2-MORPHOLINECAR-BOXAMIDE;
4-[[4-(METHYLTHIO)PHENYL]METHYL]-N-[3-(4-PY-RIDINYL)-1H-INDAZOL-5-YL]-2-MORPHOLIN-ECARBOXAMIDE;
4-[(2-METHOXYPHENYL)METHYL]-N-[3-(4-PYRIDI-NYL)-1H-INDAZOL-5-YL]-2-MORPHOLINECAR-BOXAMIDE;
4-(PHENYLMETHYL)-N-[3-(4-PYRIDINYL)-1H-INDA-ZOL-5-YL]-2-THIOMORPHOLINECARBOXAMIDE;
4-[(2-CHLORO-6-FLUOROPHENYL)METHYL]-N-[3-(4-PYRIDINYL)-1H-INDAZOL-5-YL]-2-MORPHOLI-NECARBOXAMIDE;
4-[(2-FLUORO-4-METHOXYPHENYL)METHYL]-N-[3-(4-PYRIDINYL)-1H-INDAZOL-5-YL]-2-MORPHOLI-NECARBOXAMIDE;
4-[[2-FLUORO-6-(TRIFLUOROMETHYL)PHENYL]ME-THYL]-N-[3-(4-PYRIDINYL)-1H-INDAZOL-5-YL]-2-MORPHOLINECARBOXAMIDE;
4-[(2-FLUORO-4,5-DIMETHOXYPHENYL)METHYL]-N-[3-(4-PYRIDINYL)-1H-INDAZOL-5-YL]-2-MOR-PHOLINECARBOXAMIDE;
4-[(4-CHLORO-2-FLUOROPHENYL)METHYL]-N-[3-(4-PYRIDINYL)-1H-INDAZOL-5-YL]-2-MORPHOLI-NECARBOXAMIDE;
4-[[2-FLUORO-3-(TRIFLUOROMETHYL)PHENYL]ME-THYL]-N-[3-(4-PYRIDINYL)-1H-INDAZOL-5-YL]-2-MORPHOLINECARBOXAMIDE;
4-[[2-FLUORO-5-(TRIFLUOROMETHYL)PHENYL]ME-THYL]-N-[3-(4-PYRIDINYL)-1H-INDAZOL-5-YL]-2-MORPHOLINECARBOXAMIDE;
4-[(2,3-DIFLUOROPHENYL)METHYL]-N-[3-(4-PY-RIDINYL)-1H-INDAZOL-5-YL]-2-MORPHOLIN-ECARBOXAMIDE;
4-[(2,6-DIFLUOROPHENYL)METHYL]-N-[3-(4-PY-RIDINYL)-1H-INDAZOL-5-YL]-2-MORPHOLIN-ECARBOXAMIDE;
4-[(2,4-DIFLUOROPHENYL)METHYL]-N-[3-(4-PY-RIDINYL)-1H-INDAZOL-5-YL]-2-MORPHOLIN-ECARBOXAMIDE;
4-[(2-FLUORO-5-METHOXYPHENYL)METHYL]-N-[3-(4-PYRIDINYL)-1H-INDAZOL-5-YL]-2-MORPHOLI-NECARBOXAMIDE;
4-[(3-CHLORO-2,6-DIFLUOROPHENYL)METHYL]-N-[3-(4-PYRIDINYL)-1H-INDAZOL-5-YL]-2-MORPHO-LINECARBOXAMIDE;
4-[(2-CHLORO-3,6-DIFLUOROPHENYL)METHYL]-N-[3-(4-PYRIDINYL)-1H-INDAZOL-5-YL]-2-MORPHO-LINECARBOXAMIDE;
4-[(3-CHLORO-4-FLUOROPHENYL)METHYL]-N-[3-(4-PYRIDINYL)-1H-INDAZOL-5-YL]-2-MORPHOLI-NECARBOXAMIDE;
4-[(3,5-DICHLOROPHENYL)METHYL]-N-[3-(4-PY-RIDINYL)-1H-INDAZOL-5-YL]-2-MORPHOLIN-ECARBOXAMIDE;
4-[(2,5-DIFLUOROPHENYL)METHYL]-N-[3-(4-PY-RIDINYL)-1H-INDAZOL-5-YL]-2-MORPHOLIN-ECARBOXAMIDE;
4-PHENYL-N-[3-(4-PYRIDINYL)-1H-INDAZOL-5-YL]-3-PIPERIDINECARBOXAMIDE;

1-PHENYL-N-[3-(4-PYRIDINYL)-1H-INDAZOL-5-YL]-2-PIPERAZINECARBOXAMIDE;
5-[[[4-[(2-FLUOROPHENYL)METHYL]-2-THIOMORPHOLINYL]CARBONYL]AMINO]-N-METHYL-1H-INDAZOLE-3-CARBOXAMIDE;
N-BUTYL-5-[[[4-[(2-FLUOROPHENYL)METHYL]-2-THIOMORPHOLINYL]CARBONYL]AMINO]-1H-INDAZOLE-3-CARBOXAMIDE;
5-[[[4-[(2-FLUOROPHENYL)METHYL]-2-THIOMORPHOLINYL]CARBONYL]AMINO]-N-(PHENYLMETHYL)-1H-INDAZOLE-3-CARBOXAMIDE;
1-(2-CYANOPHENYL)-N-[3-(4-PYRIDINYL)-1H-INDAZOL-5-YL]-3-PIPERIDINECARBOXAMIDE;
1-BENZOYL-N-[3-(4-PYRIDINYL)-1H-INDAZOL-5-YL]-3-PIPERIDINECARBOXAMIDE;
4-(PHENYLMETHYL)-N-[3-(4-PYRIDINYL)-1H-INDAZOL-5-YL]-2(S)-PIPERAZINECARBOXAMIDE;
4-(PHENYLMETHYL)-N-[3-(4-PYRIDINYL)-1H-INDAZOL-5-YL]-2(R)-PIPERAZINECARBOXAMIDE;
4-[(2-FLUOROPHENYL)METHYL]-N-[3-(4-PYRIDYL)-1H-INDAZOL-5-YL]-2(S)-THIOMORPHOLINECARBOXAMIDE;
4-[(2-FLUOROPHENYL)METHYL]-N-[3-(4-PYRIDINYL)-1H-INDAZOL-5-YL]-2(R)-TIHOMORPHOLINECARBOXAMIDE;
5-PHENYL-N-[3-(4-PYRIDINYL)-1H-INDAZOL-5-YL]-3-PIPERIDINECARBOXAMIDE;
4-[(2-FLUOROPHENYL)METHYL]-N-[3-(4-PYRIDINYL)-1H-INDAZOL-5-YL]-2-THIOMORPHOLINECARBOXAMIDE, 1-OXIDE;
4-[(2-FLUOROPHENYL)METHYL]-N-[3-(4-PYRIDINYL)-1H-INDAZOL-5-YL]-2-THIOMORPHOLINECARBOXAMIDE, 1,1-DIOXIDE;
4-HYDROXY-1-(PHENYLMETHYL)-N-[3-(4-PYRIDINYL)-1H-INDAZOL-5-YL]-3-PIPERIDINECARBOXAMIDE;
8-(PHENYLMETHYL)-N-[3-(4-PYRIDINYL)-1H-INDAZOL-5-YL]-1,4-DIOXA-8-AZASPIRO[4.5]DECANE-6-CARBOXAMIDE;
1-(1-PHENYLETHYL)-N-[3-(4-PYRIDINYL)-1H-INDAZOL-5-YL]-3(S)-PIPERIDINECARBOXAMIDE;
1-(PHENYLMETHYL)-N-[3-(4-PYRIDINYL)-1H-INDAZOL-5-YL]-3(R)-PYRROLIDINECARBOXAMIDE;
1-[(2-FLUOROPHENYL)METHYL]-3-(METHYLTHIO)-N-[3-(4-PYRIDINYL)-1H-INDAZOL-5-YL]-3-PYRROLIDINECARBOXAMIDE;
1-(PHENYLMETHYL)-N-[3-(4-PYRIDINYL)-1H-INDAZOL-5-YL]-3-PYRROLIDINECARBOXAMIDE;
1-[(2-FLUOROPHENYL)METHYL]-N-[3-(4-PYRIDINYL)-1H-INDAZOL-5-YL]-3-PYRROLIDINECARBOXAMIDE;
3-(HYDROXYMETHYL)-1-(PHENYLMETHYL)-N-[3-(4-PYRIDINYL)-1H-INDAZOL-5-YL]-3-PIPERIDINECARBOXAMIDE;
4-(3-PHENYLPROPYL)-N-[3-(4-PYRIDINYL)-1H-INDAZOL-5-YL]-2-THIOMORPHOLINECARBOXAMIDE;
4-(2-PHENYLETHYL)-N-[3-(4-PYRIDINYL)-1H-INDAZOL-5-YL]-2-THIOMORPHOLINECARBOXAMIDE; and
1-METHYL-5-(PHENYLMETHYL)-N-[3-(4-PYRIDINYL)-1H-INDAZOL-5-YL]-3-PIPERIDINECARBOXAMIDE;
or a pharmaceutically acceptable salt, solvate or ester thereof.

In another embodiment, the compound of Formula I is selected from the group consisting of:

4-[(2-CHLOROPHENYL)METHYL]-N-[3-(4-PYRIDINYL)-1H-INDAZOL-5-YL]-2-THIOMORPHOLINECARBOXAMIDE;
4-(4-FLUOROPHENYL)-N-[3-(4-PYRIDINYL)-1H-INDAZOL-5-YL]-3-PIPERIDINECARBOXAMIDE;
1-(2-CYANOPHENYL)-N-[3-(4-PYRIDINYL)-1H-INDAZOL-5-YL]-3-PIPERIDINECARBOXAMIDE;
4-[(2-BROMOPHENYL)METHYL]-N-[3-(4-PYRIDINYL)-1H-INDAZOL-5-YL]-2-MORPHOLINECARBOXAMIDE;
1-[(2-FLUOROPHENYL)METHYL]-N-[3-(4-PYRIDINYL)-1H-INDAZOL-5-YL]-3-PYRROLIDINECARBOXAMIDE;
4-[(2-CHLORO-6-FLUOROPHENYLMETHYL]-N-[3-(4-PYRIDINYL)-1H-INDAZOL-5-YL]-2-MORPHOLINECARBOXAMIDE;
4-[(2-FLUOROPHENYL)METHYL]-N-[3-(4-PYRIDINYL)-1H-INDAZOL-5-YL]-2(S)-THIOMORPHOLINECARBOXAMIDE;
N-[3-(4-PYRIDINYL)-1H-INDAZOL-5-YL]-4-(4-THIAZOLYLMETHYL)-2-THIOMORPHOLINECARBOXAMIDE;
4-(PHENYLMETHYL)-N-[3-(4-PYRIDINYL)-1H-INDAZOL-5-YL]-2-MORPHOLINECARBOXAMIDE;
1-[(2-CHLOROPHENYL)METHYL]-N-[3-(4-PYRIDINYL)-1H-INDAZOL-5-YL]-3-PIPERIDINECARBOXAMIDE;
1-(PHENYLMETHYL)-N-[3-(4-PYRIDINYL)-1H-INDAZOL-5-YL]-3-PIPERIDINECARBOXAMIDE;
1-METHYL-5-(PHENYLMETHYL)-N-[3-(4-PYRIDINYL)-1H-INDAZOL-5-YL]-3-PIPERIDINECARBOXAMIDE;
4-[(2-FLUOROPHENYL)METHYL]-N-[3-(4-PYRIDINYL)-1H-INDAZOL-5-YL]-2-THIOMORPHOLINECARBOXAMIDE, 1-OXIDE;
4-[(2-FLUOROPHENYL)METHYL]-N-[3-(4-PYRIDINYL)-1H-INDAZOL-5-YL]-2(R)-THIOMORPHOLINECARBOXAMIDE;
4-[(2-FLUOROPHENYL)METHYL]-N-[3-(4-PYRIDINYL)-1H-INDAZOL-5-YL]-2-THIOMORPHOLINECARBOXAMIDE, 1,1-DIOXIDE;
4-(PHENYLMETHYL)-N-[3-(4-PYRIDINYL)-1H-INDAZOL-5-YL]-2(R)-PIPERAZINECARBOXAMIDE;
4-[(2-FLUOROPHENYL)METHYL]-N-[3-(4-PYRIDINYL)-1H-INDAZOL-5-YL]-2-MORPHOLINECARBOXAMIDE;
4-[(2-CHLOROPHENYL)METHYL]-N-[3-(4-PYRIDINYL)-1H-INDAZOL-5-YL]-2-MORPHOLINECARBOXAMIDE;
1-[(2-FLUOROPHENYL)METHYL]-N-[3-(4-PYRIDINYL)-1H-INDAZOL-5-YL]-3-PIPERIDINECARBOXAMIDE; and
4-[(2-FLUOROPHENYL)METHYL]-N-[3-(4-PYRIDINYL)-1H-INDAZOL-5-YL]-2-THIOMORPHOLINECARBOXAMIDE;
or a pharmaceutically acceptable salt, solvate of ester thereof.

In another embodiment, the compound of formula I is selected from the group consisting of:
1-METHYL-5-(PHENYLMETHYL)-N-[3-(4-PYRIDINYL)-1H-INDAZOL-5-YL]-3-PIPERIDINECARBOXAMIDE;
4-[(2-FLUOROPHENYL)METHYL]-N-[3-(4-PYRIDINYL)-1H-INDAZOL-5-YL]-2-THIOMORPHOLINECARBOXAMIDE, 1-OXIDE;

4-[(2-FLUOROPHENYL)METHYL]-N-[3-(4-PYRIDI-NYL)-1H-INDAZOL-5-YL]-2(R)-THIOMORPHOLIN-ECARBOXAMIDE;

4-[(2-FLUOROPHENYL)METHYL]-N-[3-(4-PYRIDI-NYL)-1H-INDAZOL-5-YL]-2-THIOMORPHOLIN-ECARBOXAMIDE, 1,1-DIOXIDE;

4-(PHENYLMETHYL)-N-[3-(4-PYRIDINYL)-1H-INDA-ZOL-5-YL]-2(R)-PIPERAZINECARBOXAMIDE;

4-[(2-FLUOROPHENYL)METHYL]-N-[3-(4-PYRIDI-NYL)-1H-INDAZOL-5-YL]-2-MORPHOLINECAR-BOXAMIDE;

4-[(2-CHLOROPHENYL)METHYL]-N-[3-(4-PYRIDI-NYL)-1H-INDAZOL-5-YL]-2-MORPHOLINECAR-BOXAMIDE;

1-[(2-FLUOROPHENYL)METHYL]-N-[3-(4-PYRIDI-NYL)-1H-INDAZOL-5-YL]-3-PIPERIDINECAR-BOXAMIDE; and 4-[(2-FLUOROPHENYL)METHYL]-N-[3-(4-PYRIDI-NYL)-1H-INDAZOL-5-YL]-2-THIOMORPHOLIN-ECARBOXAMIDE;

or a pharmaceutically acceptable salt, solvate of ester thereof.

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the teuu "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, nuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancreas, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compounds, compositions and methods of the invention include breast and prostate.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Speicific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chaitreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-rnethylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L- glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamie acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type T (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-a, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134, 142, 5,380,738, 5,393,790, 5,466,823, 5,633,272 and 5,932, 598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenypamino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-ypoxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjuctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94102461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenypethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, CI1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with potassium salts, magnesium salts, beta-blockers (such as atenolol) and endothelin-a (ETa) antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors.

A compound of the instant invention may be used in combination with a chemotherapeutic agent selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

Examples of such chemotherapeutic agents include:

(1) taxanes such as paclitaxel (TAXOL®) and/or docetaxel (Taxotere®);

(2) platinum coordinator compounds, such as, for example, carboplatin, cisplatin and oxaliplatin (e.g. Eloxatin);

(3) EGF inhibitors that are antibodies, such as: HER2 antibodies (such as, for example trastuzumab (Herceptin®, Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva™ (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1C11 (ImClone Systems), DC 101 (a KDR VEGF Receptor 2 from ImClone Systems);

(6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals);

(7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);

(8) anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda);

(9) epothilones such as BMS-247550 (Bristol-Myers Squibb), and EPO906 (Novartis Pharmaceuticals);

(10) topoisomerase inhibitors such as topotecan (Glaxo SmithKline), and Camptosar (Pharmacia);

(11) vinca alkaloids, such as, navelbine (Anvar and Fabre, France), vincristine and vinblastine;

(12) antibodies that are inhibitors of αVβ3 integrins, such as, LM-609 (see, Clinical Cancer Research, Vol. 6, page 3056-3061, August 2000, the disclosure of which is incorporated herein by reference thereto);

(13) folate antagonists, such as Methotrexate (MTX), and Premetrexed (Alimta);

(14) ribonucleotide reductase inhibitors, such as Hydroxyurea (HU);

(15) anthracyclines, such as Daunorubicin, Doxorubicin (Adriamycin), and Idarubicin;

(16) biologics, such as interferon (e.g., Intron-A and Roferon), pegylated interferon (e.g., Peg-Intron and Pegasys), and Rituximab (Rituxan, antibody used for the treatment of non-Hodgkin's lymphoma);

(17) thalidomide (or related imid);

(18) Bcr/abl kinase inhibitors, such as, for example Gleevec (STI-571), AMN-17, ONO12380, SU11248 (Sunitinib) and BMS-354825

(19) MEK1 and/or MEK2 inhibitors, such as PD0325901 and Arry-142886 (AZD6244);

(20) IGF-1 and IGF-2 inhibitors that are small molecules, such as, for example, NVP-AEW541;

(21) small molecule inhibitors of RAF and BRAT kinases, such as, for example, BAY 43-9006 (Sorafenib);

(22) small molecule inhibitors of cell cycle dependent kinases such as CDK1, CDK2, CDK4 and CDK6, such as, for example, CYC202, BMS387032, and Flavopiridol;

(23) alkylating agents, such as, for example, Temodar® brand of temozolomide;

(24) farnesyl protein transferase inhibitors, such as, for example:

(a) Sarasar® brand of lonifarnib (i.e., 4-[2-[4-(3,10-dibromo-8-chloro-6,11-dihydro-5H-benzo[5,6]cyclohepta[1,2-b]byridin-11-yl)-1-piperidinyl)-2-oxoethyl]-1-piperidinecarboxamide, see for example, U.S. Pat. No. 5,874,442 issued Feb. 23, 1999, and U.S. Pat. No. 6,632,455 issued Oct. 14, 2003 the disclosures of each being incorporated herein by reference thereto), (b) Zarnestra® brand of tipifarnib (i.e., (R)-6-amino[(4-chlorophenyl)(1-methyl-1H-imidazol-5-yl)methyl]-4-(3-chlorophenyl)-1-methyl-2(1H)-quinolinone, see for example, WO 97/16443 published May 9, 1997 and U.S.

Pat. No. 5,968,952 issued Oct. 19, 1999, the disclosures of each being incorporated herein by reference thereto), and (c) Bristol-Myers Squibb 214662:

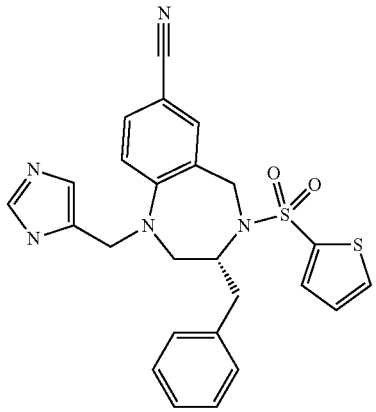 [SMILES: N#Cc1ccc2c(c1)CN(S(=O)(=O)c1cccs1)[C@H](Cc1ccccc1)CN2Cc1cnc[nH]1]

(see WO97/30992 published Aug. 28, 1997, U.S. Pat. No. 6,011,029 issued Jan. 4, 2000, and U.S. Pat. No. 6,455,523, the disclosures of each being incorporated herein by reference thereto).

The Bcr/abl kinase inhibitors, EGF receptor inhibitors, and HER-2 antibodies (EGF receptor inhibitors that are antibodies) described above are also known as signal transduction inhibitors. Therefore, chemotherapeutic agents, as used herein, include signal transduction inhibitors.

Typical signal transduction inhibitors, that are chemotherapeutic agents, include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

A compound of the instant invention may also be useful for treating cancer in combination with the following chemotherapeutic agents: abarelix (Plenaxis depot®); aldesleukin (Prokine®); Aldesleukin (Proleukin ®); Alemtuzumabb (Campath®); alitretinoin (Panretin®); allopurinol (Zyloprim®); altretamine (Hexalen ®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet ®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere ®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®) Elliott's B Solution (Elliott's B Solution®); eltrombopag (Promacta®); epirubicin (Ellence®); Epoetin alfa (epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Ilistrelin implant®); hydroxyurea (Hydrea®); Ibritumomab Tiuxetan (Zevalin®); idarubicin (Idamycin®); Ifosfamide (IFEX ®); irnatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista ®); Rituximab (Rituxan®); Ridaforolimus; romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742); the disclosures of which is incorporated herein by reference thereto.

For example, the compounds of formula I can be administered orally (e.g., as a capsule), and the chemotherapeutic agents can be administered intravenously, usually as an intravenous (IV) solution. The use of a pharmaceutical composition comprising more than one drug is within the scope of this invention.

The compound of formula I and the chemotherapeutic agents are administered in therapeutically effective dosages to obtain clinically acceptable results, e.g., reduction or elimination of symptoms or of the tumor. Thus, the compound of formula I and chemotherapeutic agents can be administered concurrently or consecutively in a treatment protocol. The administration of the chemotherapeutic agents can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

The compounds of this invention and chemotherapeutic agents can be administered in a treatment protocol that usually lasts one to seven weeks, and is repeated typically from 6 to 12 times. Generally the treatment protocol can last one to four weeks. Treatment protocols of one to three weeks can also be used. A treatment protocol of one to two weeks can also be used. During this treatment protocol or cycle the compounds of this invention can be administered daily while the chemotherapeutic agents can be administered one or more times a week. Generally, a compound of this invention can be administered daily (i.e., once per day), and in one embodiment twice per day, and the chemotherapeutic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or intrathecally or some suitable combination(s) thereof.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow TV infusion over 10-20 minutes every 3 to 4 weeks; (x) for the biologic interferon (intron-A, Roferon) 5 to 20 million 11.3 three times per week; (y) for the biologic pegylated interferon (Peg-intron, Pegasys) 3 to 4 micrograms/kg/day chronic sub cutaneous (until relapse or loss of activity); (z) for the biologic Rituximab (Rituxan) (antibody used for non-Hodgkin's lymphoma) 200-400 mg/m$^2$ IV weekly over 4-8 weeks for 6 months; (aa) for the alkylating agent temozolomide 75 mg/m$^2$ to 250mg/m$^2$, for example, 150 mg/m$^2$, or for example, 200 mg/m$^2$, such as 200 mg/m$^2$ for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imids) can be used orally in amounts of about 200 to about 800 mg/day, and can be contiuously dosed or used until releapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

The PPT inhibitor Sarasar® (brand of lonifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®., for example, can be administered once per week in an amount of about 50 to about 100 mg/m$^2$ and in another example about 60 to about 80 mg/m$^2$. In another example Paclitaxel (e.g., Taxol®. can be administered once every three weeks in an amount of about 150 to about 250 mg/m$^2$ and in another example about 175 to about 225 mg/m$^2$.

In another example, Docetaxel (e.g., Taxotere®) can be administered once per week in an amount of about 10 to about 45 mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula I and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of an chemotherapeutic agent according to the individual patient's needs, as the treatment proceeds. All such modifications are within the scope of the present invention.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of the invention can be made according to the processes described below.

Commonly Used Abbreviations
ACN Acetonitrile
AcOH Acetic acid
DAST (diethylamino)sulfur trifluoride
DCC Dicyclohexylcarbodiimide
DCU Dicyclohexylurea
DCM Dichloromethane
DIAD Diisopropylazodicarboxylate
DIEA Diisopropylethylamine
DMAP 4-Dimethylaminopyridine
DME Dimethoxyethane
DMF Dimethylformamide
DMFDMA N,N-Dimethylformamide dimethylacetal
DMSO Dimethyl sulfoxide
DTT Dithiothreitol
EDCI 1-(3-dimethylamino-propyl)-3-ethylcarbodiimide hydrochloride
EtOAc Ethyl acetate
EtOH Ethanol
HATU N,N,N',N'-Tetramethyl-O-(7-Azabenzotriazol-1-yl) Uronium hexafluorophosphate H₂O water Hex hexanes HOBt 1-Hydroxylbenzotriazole HPLC High pressure liquid chromatography LCMS Liquid chromatography mass spectrometry LDA Lithium diisopropylamide mCPBA meta-Chloroperoxybenzoic acid MeOH Methanol MTT (3-[4,5-dimethyl-thiazol-2-yl]-2,5-diphenyltetrazolium bromide, Thiazolyl blue)

NaH Sodium hydride

NMR Nuclear magnetic resonance

PFP Pentafluorophenol

PMB p-methoxybenzyl

Pyr Pyridine

RT Room temperature

SEMCl 2-(Trimethylsily)ethoxy methyl chloride

TEA Triethylamine

Tr Triphenyl methane

TrCl Triphenyl methane chloride

TFA Trifluoroacetic acid

THF Tetrahydrofuran

TLC Thin layer chromatography

TMS Trimethylsilyl

Analytical Method

The LCMS conditions are: (1) column: C-18 reverse phase, 5 um, 4.6×50 mm, (2) MS:PE Sciex API-150EX, and (3) HPLC: Shimadzu LC-10 ADvp, 1 ml/min, linerar gradient 10% acetonitirle in water to 95% acetonitrile in water, both contain 0.05% TFA Compound Synthesis The compounds of this invention can be made according to the processes described in the schemes below.

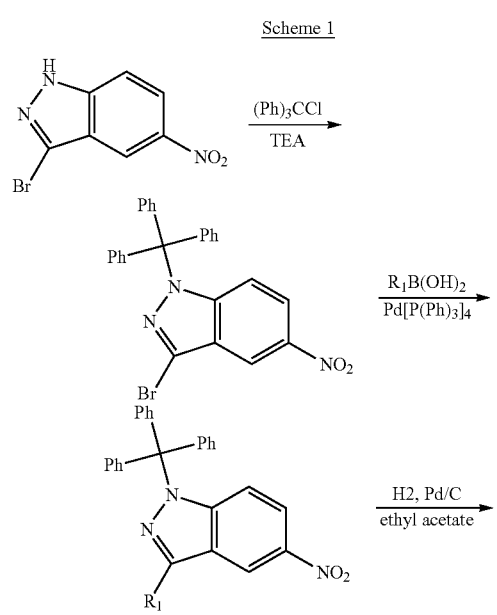

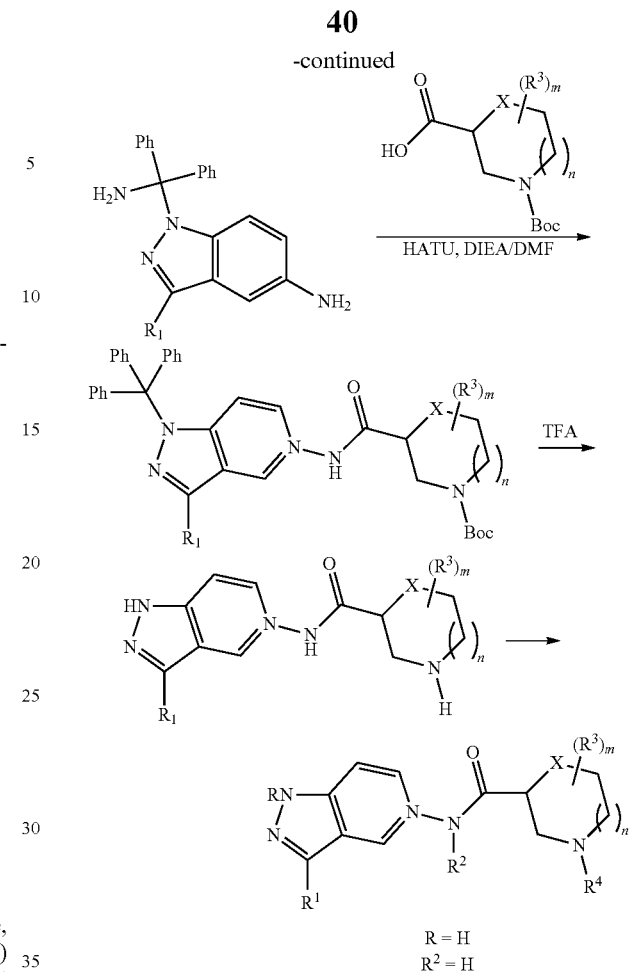

5-Nitro-3-(pyridin-4-yl)-1-trityl-1H-indazole

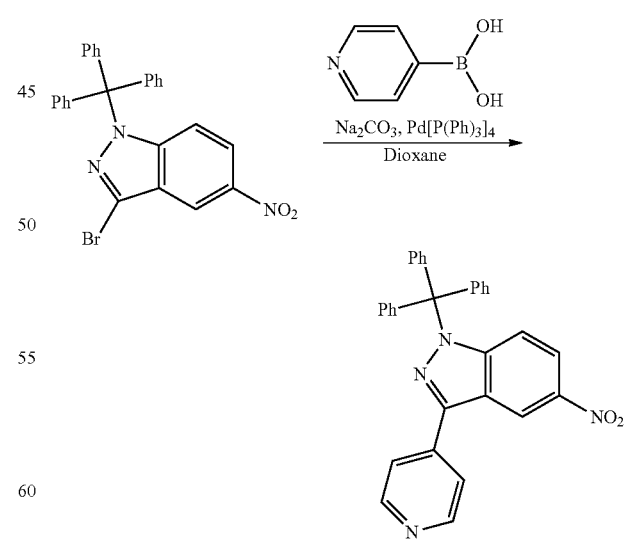

3-Bromo-5-nitro-1-trityl-1H-indazole (1 g, 0.002 mol) was added to a vial containing pyridin-4-ylboronic acid (0.279 g, 0.00227 mol) and tetrakis(triphenylphosphine)-palladium (0.1155 g, 0.0001 mol). After purging the vial with nitrogen gas, dioxane (6 L) and 2M sodium carbonate (0.006 mol) was added to the vial respectively. The reaction mixture was stirred and was heated to 80° C. for 16 h. Upon completion, the mixture was concentrated under vacuo. Water (3 mL) was added and was extracted using dichloromethane (3×3 mL). The extracts were combined and dried using anhydrous sodium sulfate. The resulting suspension was filtered and concentrated. The crude product was purified using flash chromatography (1:1 Hexane:Ethyl Acetate). Pure product (0.8954 g, 92.8% yield) was recovered.

Similar compounds with varying left-hand-side substitutions were made using the procedure above with slight modifications to the type of boronic acid used.

3-(Pyridin-4-yl)-1-trityl-1H-indazol-5-amine

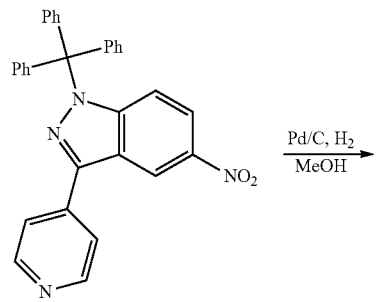

To 5-nitro-3-(pyridin-4-yl)-1-trityl-1H-indazole (0.8954 g, 0.00185 mol), 10% activated palladium on carbon (0.8954 g, 1 eq by weight) was added. The reaction flask was put under vacuum, and methanol (18.5 mL) and ethyl acetate (2 mL) was added. Hydrogen gas was bubbled through the reaction for 15 minutes. The reaction was stirred at room temperature for and additional 16 h. The reaction was filtered through celite and concentrated under vacuo. The crude product (0.819 g, 95% yield) was progressed to the next step without further purification.

4-Benzyl-N-(3-(pyridin-4-yl)-1-trityl-1H-indazol-5-yl)morpholine-2-carboxamide

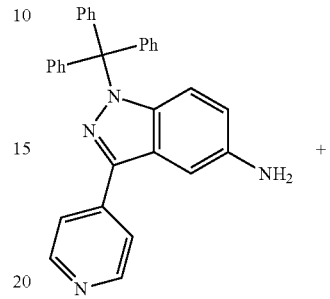

+

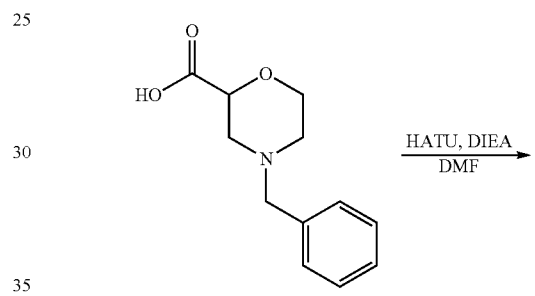

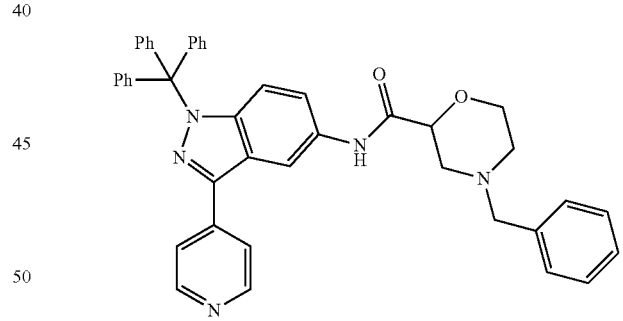

2-(7-Aza-1H-benzotriazole-1-yl)-1,1,3,3-tetramethyluronium hexafluorophosphate (HATU) (0.019 g, 0.04976 mmol) and Diisopropyl ethyl amine (DIEA) (0.0116 mL) was added to a suspension of 4-benzylmorpholine-2-carboxylic acid (0.0086 g, 0.0332 mmol) in DMF (0.183 mL and was stirred at room temperature for 15 minutes. A solution of 3-(pyridin-4-yl)-1-trityl-1H-indazol-5-amine (0.015 g, 0.0332 mmol) in DMF (0.100 mL) was added to the reaction and was stirred at room temperature for an additional 30 minutes. The reaction was quenched with water (1 mL) and extracted with ethyl acetate (3×1 mL). The extracts were combined, dried using anhydrous sodium sulfate, filtered, and concentrated in vacuo. The crude product was progressed to the next step without purification.

Similar compounds with varying right-hand-side substitutions were made using the procedure above with slight modifications to the type of carboxylic acid used.

4-Benzyl-N-(3-(pyridin-4-yl)-1H-indazol-5-yl)morpholine-2-carboxamide

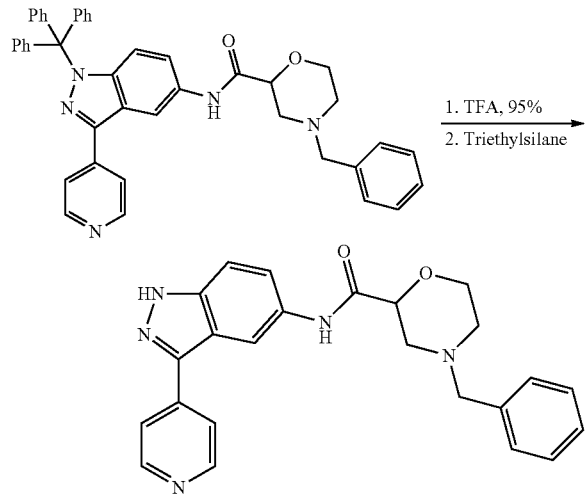

Trifluoroacetic acid (1 mL) was added to 4-benzyl-N-(3-(pyridin-4-yl)-1-trityl-1H-indazol-5-yl)morpholine-2-carboxamide (0.0217 g, 0.0332 mmol). The reaction was stirred at room temperature for 30 minutes. Triethylsilane (0.1 mL) was added to the reaction and stirred for an additional 5 minutes. The reaction was concentrated in vacuo and purified using prep LC/MS. LC-MS: 414.26 [M+H]. LC/MS RT=1.99 min.

N-(3-(pyridin-4-yl)-1H-indazol-5-yl)morpholine-2-carboxamide

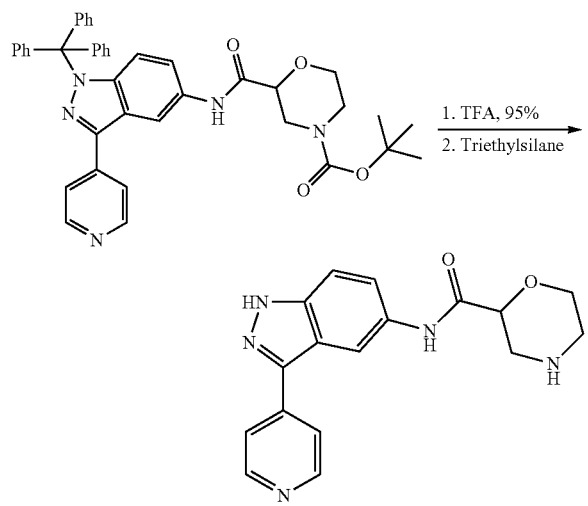 [SMILES: CC(C)(C)OC(=O)N1CCOC(C(=O)Nc2ccc3c(c2)c(-c2ccncc2)nn3C(c2ccccc2)(c2ccccc2)c2ccccc2)C1 ; O=C(Nc1ccc2[nH]nc(-c3ccncc3)c2c1)C1CNCCO1]

Trifluoroacetic acid (1mL) was added to N-(3-(pyridin-4-yl)-1H-indazol-5-yl)morpholine-2-carboxamide (0.201 g, 0.487 mmol) and was stirred at room temperature for 30 minutes. Triethylsilane (0.1 mL) was added to the reaction and stirred for an additional 5 minutes. The reaction was concentrated in vacuo, and the crude product was progress to the next step without further purification.

4-(2-Fluorobenzyl)-N-(3-(pyridin-4-yl)-1H-indazol-5-yl)morpholine-2-carboxamide

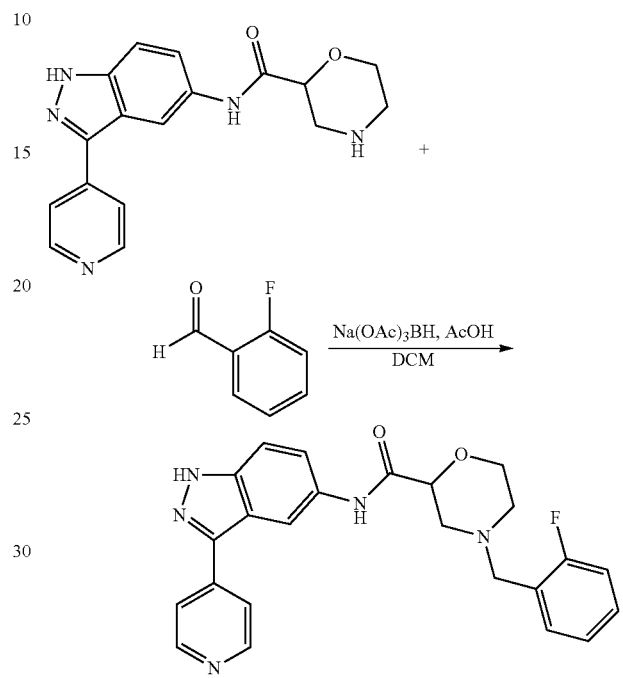

In a flask, dichloromethane (0.5 mL) and acetic acid (3drops) was added to N-(3-(pyridin-4-yl)-1H-indazol-5-yl)morpholine-2-carboxamide (0.014 g, 0.0443 mmol) and 2-fluorobenzaldehyde (0.0112 g, 0.09 mmol). The reaction was stirred for 15 minutes. Sodium triacetoxyborohydride (0.040 g, 0.177 mmol) was added in one portion. The reaction was stirred for an additional 16 hours. Saturated sodium bicarbarbonate (1 mL) was added. The reaction was stirred for an additional 5 minutes and was extracted with dichloromethane (3×1 mL). The extracts were combined, dried with anhydrous sodium sulfate, filtered, and concentrated in vacuo. The resulting crude product was purified by prep LC/MS. LC-MS: 432.2 [M+H]. LC/MS RT0.869 min.

1-Benzoyl-N-(3-(pyridin-4-yl)-1H-indazol-5-yl)piperidine-3-carboxamide

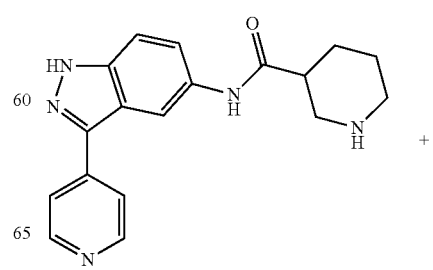

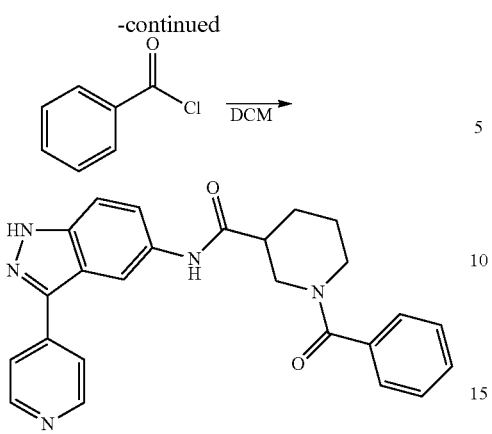

In a flask, dichloromethane (0.023 mL) was added to benzoyl chloride. The reaction was cooled to 0° C., and a solution of N-(3-(pyridin-4-yl)-1H-indazol-5-yl)piperidine-3-carboxamide (0.014 g, 0.044 mmol) in dichloromethane (0.020 mL) was dropwise added to the benzoyl chloride solution. The reaction stirred for 6 hrs from 0° C. to room temperature. The reaction was quenched with water (1 mL) and extracted with dichloromethane (3×1 mL). The extracts were combined and dried with sodium sulfate. The crude product was purified using prep LC/MS. LC-MS: 426.1 [M+H]. LC/MS RT=2.998 min.

Following compounds were prepared using the procedure described above.

| Compd # | Structure | Chemical Names | TdF Kd (nM) | cERK2 IC50 (nM) | aERK2 IC50 (nM) | Calc. Mass | Obs. M+H | Retention time 10 min method (min.) |
|---|---|---|---|---|---|---|---|---|
| 1 | 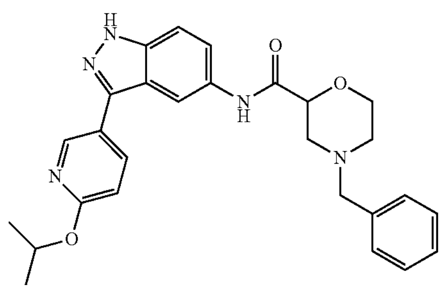 [SMILES: CC(C)Oc1ccc(-c2n[nH]c3ccc(NC(=O)C4CN(Cc5ccccc5)CCO4)cc23)cn1] | N-[3-[6-(1-METHYLETHOXY)-3-PYRIDINYL]-1H-INDAZOL-5-YL]-4-(PHENYLMETHYL)-2-MORPHOLINE-CARBOXAMIDE | 240 | 532.1 | 1000.0 | 471.2 | 472.3 | 3.53 |
| 2 | 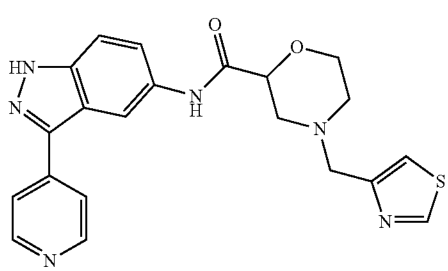 | N-[3-(4-PYRIDINYL)-1H-INDAZOL-5-YL]-4-(4-THIAZOLYL-METHYL)-2-MORPHOLINE-CARBOXAMIDE | 546 | 1839.2 | 583.0 | 420.1 | 421.10 | 0.711 |
| 3 | 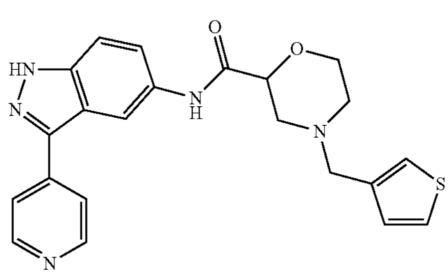 [SMILES: O=C(Nc1ccc2[nH]nc(-c3ccncc3)c2c1)C1CN(Cc2ccsc2)CCO1] | N-[3-(4-PYRIDINYL)-1H-INDAZOL-5-YL]-4-(3-THIENYLMETHYL)-2-MORPHOLINE-CARBOXAMIDE | 77 | 87.6 | | 419.1 | 420.18 | 0.803 |

-continued

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 4 | 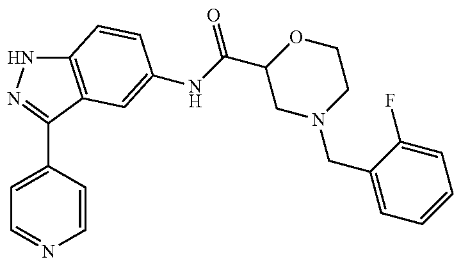 [SMILES: O=C(Nc1ccc2[nH]nc(-c3ccncc3)c2c1)C1CN(Cc2ccccc2F)CCO1] | 4-[(2-FLUOROPHENYL)METHYL]-N-[3-(4-PYRIDINYL)-1H-INDAZOL-5-YL]-2-MORPHOLINE-CARBOXAMIDE | 20 | 29.3 | 20.7 | 431.2 | 432.20 | 0.869 |
| 5 | 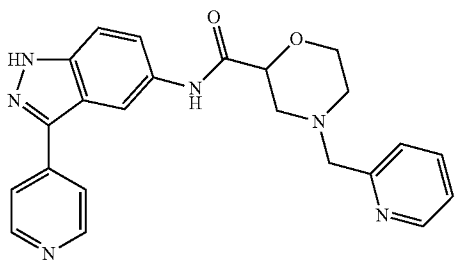 [SMILES: O=C(Nc1ccc2[nH]nc(-c3ccncc3)c2c1)C1CN(Cc2ccccn2)CCO1] | N-[3-(4-PYRIDINYL)-1H-INDAZOL-5-YL]-4-(2-PYRIDINYL-METHYL)-2-MORPHOLINE-CARBOXAMIDE | 647 | 2444.4 | 1071.1 | 414.2 | 415.20 | 0.748 |
| 6 | 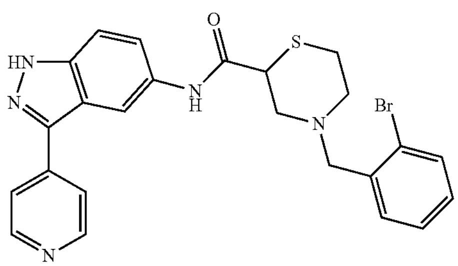 | 4-[(2-BROMOPHENYL)METHYL]-N-[3-(4-PYRIDINYL)-1H-INDAZOL-5-YL]-2-THIOMORPHOLINE-CARBOXAMIDE | 38 | 114.3 | | 507.1 | 508.28 | 2.43 |
| 7 | 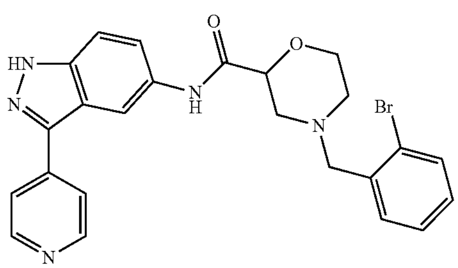 [SMILES: O=C(Nc1ccc2[nH]nc(-c3ccncc3)c2c1)C1CN(Cc2ccccc2Br)CCO1] | 4-[(2-BROMOPHENYL)METHYL]-N-[3-(4-PYRIDINYL)-1H-INDAZOL-5-YL]-2-MORPHOLINE-CARBOXAMIDE | 17 | 96.9 | | 491.1 | 492 | 2.519 |
| 8 | 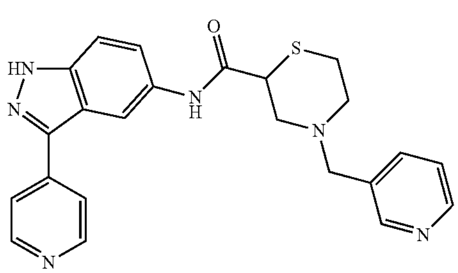 | N-[3-(4-PYRIDINYL)-1H-INDAZOL-5-YL]-4-(3-PYRIDINYL-METHYL)-2-THIOMORPHOLINE-CARBOXAMIDE | 4608 | 1066.0 | | 430.2 | 431 | 0.847 |

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 9 | 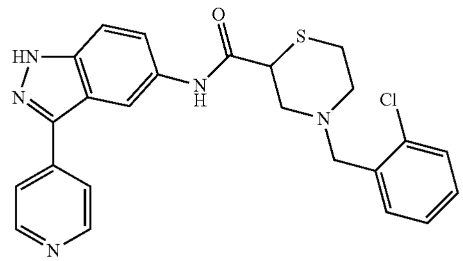 | 4-[(2-CHLOROPHENYL)METHYL]-N-[3-(4-PYRIDINYL)-1H-INDAZOL-5-YL]-2-THIOMORPHOLINE-CARBOXAMIDE | 20 | 42.4 | 54.2 | 463.1 | 464.33 | 2.37 |
| 10 | 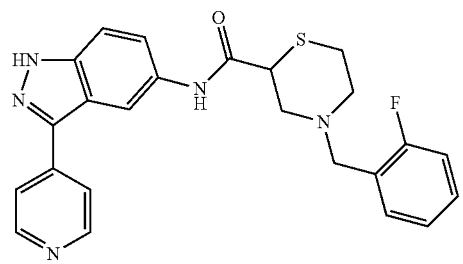 [SMILES: O=C(Nc1ccc2[nH]nc(-c3ccncc3)c2c1)C1CN(Cc2ccccc2F)CCS1] | 4-[(2-FLUOROPHENYL)METHYL]-N-[3-(4-PYRIDINYL)-1H-INDAZOL-5-YL]-2-THIOMORPHOLINE-CARBOXAMIDE | 15 | 36.4 | 77.2 | 447.2 | 448.31 | 2.18 |
| 11 | 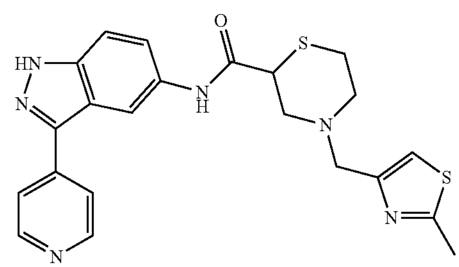 [SMILES: Cc1nc(CN2CCSC(C(=O)Nc3ccc4[nH]nc(-c5ccncc5)c4c3)C2)cs1] | 4-[(2-METHYL-4-THIAZOLYL)METHYL]-N-[3-(4-PYRIDINYL)-1H-INDAZOL-5-YL]-2-THIOMORPHOLINE-CARBOXAMIDE | 616 | 840.1 | 474.6 | 450.1 | 451.13 | 2 |
| 12 | 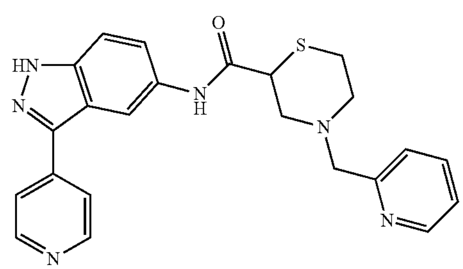 [SMILES: O=C(Nc1ccc2[nH]nc(-c3ccncc3)c2c1)C1CN(Cc2ccccn2)CCS1] | N-[3-(4-PYRIDINYL)-1H-INDAZOL-5-YL]-4-(2-PYRIDINYL-METHYL)-2-THIOMORPHOLINE-CARBOXAMIDE | 674 | 1314.4 | | 430.2 | 431.25 | 1.95 |
| 13 | 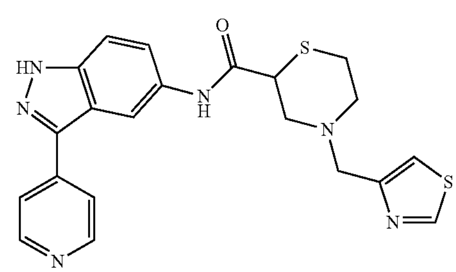 [SMILES: O=C(Nc1ccc2[nH]nc(-c3ccncc3)c2c1)C1CN(Cc2cscn2)CCS1] | N-[3-(4-PYRIDINYL)-1H-INDAZOL-5-YL]-4-(4-THIAZOLYL-METHYL)-2-THIOMORPHOLINE-CARBOXAMIDE | 201 | 929.2 | | 436.1 | 437.22 | 1.8 |

-continued

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 14 | 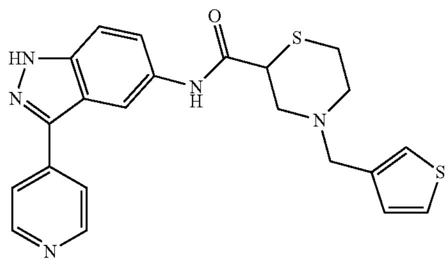 [SMILES: O=C(Nc1ccc2[nH]nc(-c3ccncc3)c2c1)C1CN(Cc2ccsc2)CCS1] | N-[3-(4-PYRIDINYL)-1H-INDAZOL-5-YL]-4-(3-THIENYLMETHYL)-2-THIOMORPHOLINE-CARBOXAMIDE | 34 | 182.7 | | 435.1 | 436.13 | 2.07 |
| 15 | 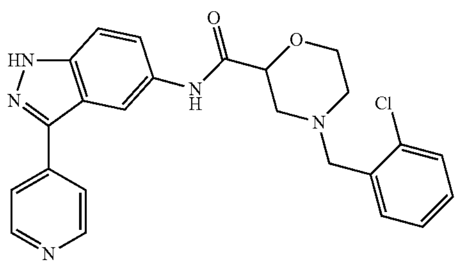 [SMILES: O=C(Nc1ccc2[nH]nc(-c3ccncc3)c2c1)C1CN(Cc2ccccc2Cl)CCO1] | 4-[(2-CHLOROPHENYL)METHYL]-N-[3-(4-PYRIDINYL)-1H-INDAZOL-5-YL]-2-MORPHOLINE-CARBOXAMIDE | 17 | 77.8 | | 447.1 | 448.18 | 2.28 |
| 16 | 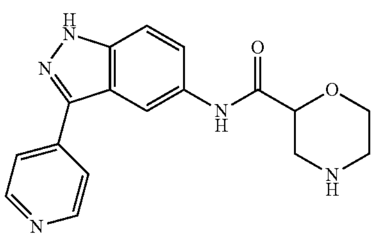 | N-[3-(4-PYRIDINYL)-1H-INDAZOL-5-YL]-2-MORPHOLINE-CARBOXAMIDE | 13486 | 2143.8 | 852.4 | 323.1 | 324.37 | 1.39 |
| 17 | 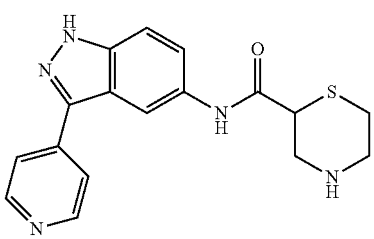 [SMILES: O=C(Nc1ccc2[nH]nc(-c3ccncc3)c2c1)C1CNCCO1] | N-[3-(4-PYRIDINYL)-1H-INDAZOL-5-YL]-2-THIOMORPHOLINE-CARBOXAMIDE | 5628 | 109.2 | 124.1 | 339.1 | 340.18 | 1.54 |
| 18 | 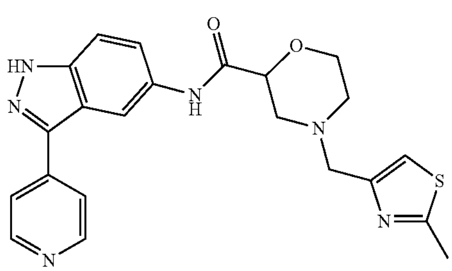 [SMILES: Cc1nc(CN2CCOC(C(=O)Nc3ccc4[nH]nc(-c5ccncc5)c4c3)C2)cs1] | 4-[(2-METHYL-4-THIAZOLYL)METHYL]-N-[3-(4-PYRIDINYL)-1H-INDAZOL-5-YL]-2-MORPHOLINE-CARBOXAMIDE | 571 | 1166.9 | 18122.9 | 434.2 | 435.26 | 2.2 |

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 19 | 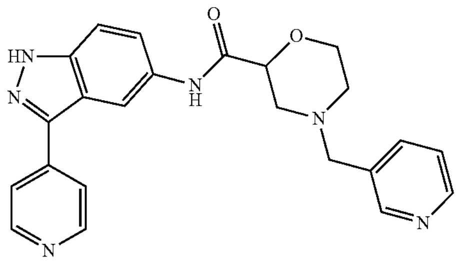 [SMILES: O=C(Nc1ccc2[nH]nc(-c3ccncc3)c2c1)C1CN(Cc2cccnc2)CCO1] | N-[3-(4-PYRIDINYL)-1H-INDAZOL-5-YL]-4-(3-PYRIDINYL-METHYL)-2-MORPHOLINE-CARBOXAMIDE | 517 | 2200.9 | 17040.2 | 414.2 | 415.33 | 1.92 |
| 20 | 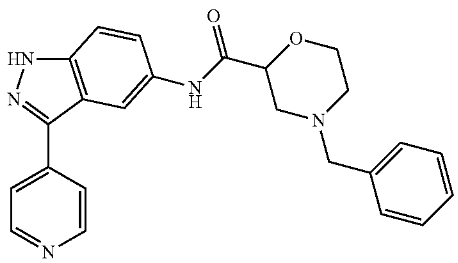 | 4-(PHENYLMETHYL)-N-[3-(4-PYRIDINYL)-1H-INDAZOL-5-YL]-2-MORPHOLINE-CARBOXAMIDE | 10 | 51.1 | | 413.2 | 414.23 | 1.99 |
| 21 | 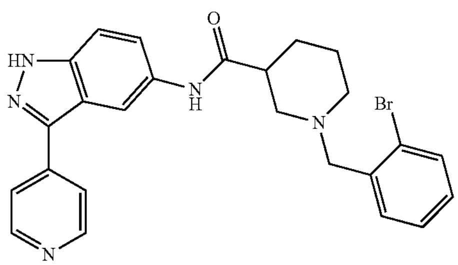 [SMILES: O=C(Nc1ccc2[nH]nc(-c3ccncc3)c2c1)C1CCCN(Cc2ccccc2Br)C1] | 1-[(2-BROMOPHENYL)METHYL]-N-[3-(4-PYRIDINYL)-1H-INDAZOL-5-YL]-3-PIPERIDINE-CARBOXAMIDE | 4 | 130.1 | | 489.1 | 490 | 2.562 |
| 22 | 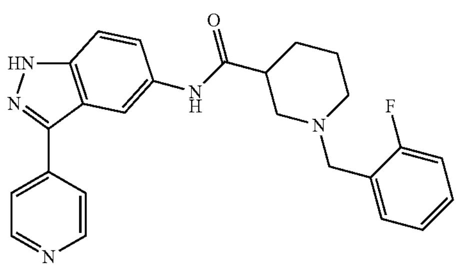 | 1-[(2-FLUOROPHENYL)METHYL]-N-[3-(4-PYRIDINYL)-1H-INDAZOL-5-YL]-3-PIPERIDINE-CARBOXAMIDE | 9 | 27.3 | | 429.2 | 430.1 | 2.322 |
| 23 | 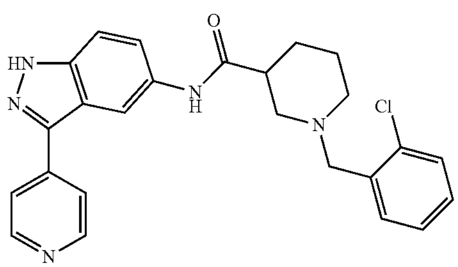 [SMILES: O=C(Nc1ccc2[nH]nc(-c3ccncc3)c2c1)C1CCCN(Cc2ccccc2Cl)C1] | 1-[(2-CHLOROPHENYL)METHYL]-N-[3-(4-PYRIDINYL)-1H-INDAZOL-5-YL]-3-PIPERIDINE-CARBOXAMIDE | 3 | 157.9 | | 445.2 | 446.1 | 2.508 |

-continued

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 24 | 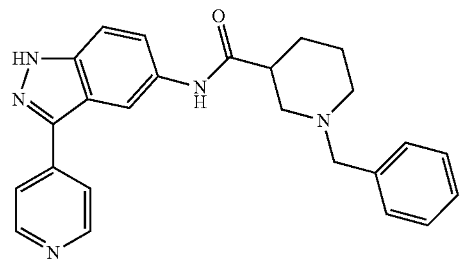 [SMILES: O=C(Nc1ccc2[nH]nc(-c3ccncc3)c2c1)C1CCCN(Cc2ccccc2)C1] | 1-(PHENYLMETHYL)-N-[3-(4-PYRIDINYL)-1H-INDAZOL-5-YL]-3-PIPERIDINE-CARBOXAMIDE | 20 | 239.5 | | 411.2 | 412.1 | 2.322 |
| 25 | 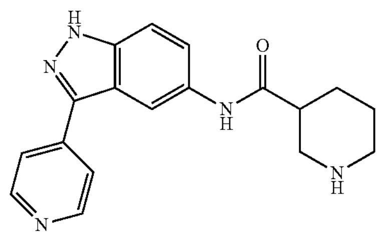 | N-[3-(4-PYRIDINYL)-1H-INDAZOL-5-YL]-3-PIPERIDINE-CARBOXAMIDE | 4500 | 631.4 | | 321.2 | 322.33 | 1.65 |
| 26 | 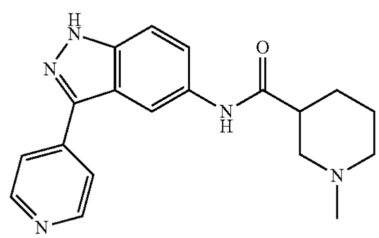 [SMILES: CN1CCCC(C(=O)Nc2ccc3[nH]nc(-c4ccncc4)c3c2)C1] | 1-METHYL-N-[3-(4-PYRIDINYL)-1H-INDAZOL-5-YL]-3-PIPERIDINE-CARBOXAMIDE | 1100 | 4866.0 | | 335.2 | 336.31 | 1.65 |
| 27 | 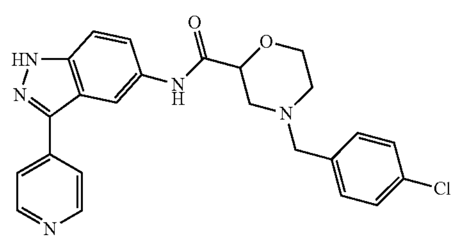 [SMILES: O=C(Nc1ccc2[nH]nc(-c3ccncc3)c2c1)C1CN(Cc2ccc(Cl)cc2)CCO1] | 4-[(4-CHLOROPHENYL)METHYL]-N-[3-(4-PYRIDINYL)-1H-INDAZOL-5-YL]-2-MORPHOLINE-CARBOXAMIDE | 3532 | 537.8 | | 447.1 | 448 | 2.544 |
| 28 | 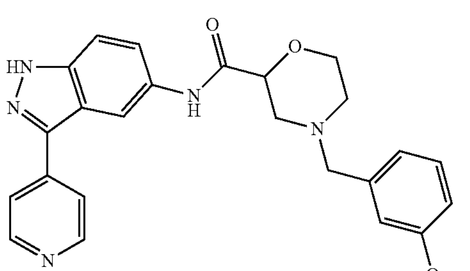 | 4-[(3-METHOXYPHENYL)METHYL]-N-[3-(4-PYRIDINYL)-1H-INDAZOL-5-YL]-2-MORPHOLINE-CARBOXAMIDE | 3617 | 289.8 | | 443.2 | 444.1 | 2.339 |

-continued

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 29 | 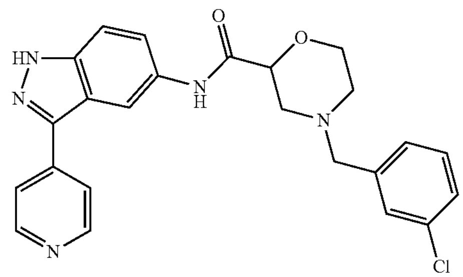 [SMILES: O=C(Nc1ccc2[nH]nc(-c3ccncc3)c2c1)C1CN(Cc2cccc(Cl)c2)CCO1] | 4-[(3-CHLOROPHENYL)METHYL]-N-[3-(4-PYRIDINYL)-1H-INDAZOL-5-YL]-2-MORPHOLINE-CARBOXAMIDE | 141 | 150.7 | 123.4 | 447.1 | 448 | 2.529 |
| 30 | 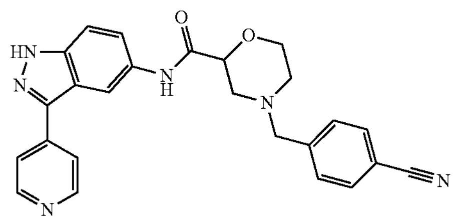 [SMILES: N#Cc1ccc(CN2CCOC(C(=O)Nc3ccc4[nH]nc(-c5ccncc5)c4c3)C2)cc1] | 4-[(4-CYANOPHENYL)METHYL]-N-[3-(4-PYRIDINYL)-1H-INDAZOL-5-YL]-2-MORPHOLINE-CARBOXAMIDE | 3293 | 1282.2 | | 438.2 | 439.1 | 2.17 |
| 31 | 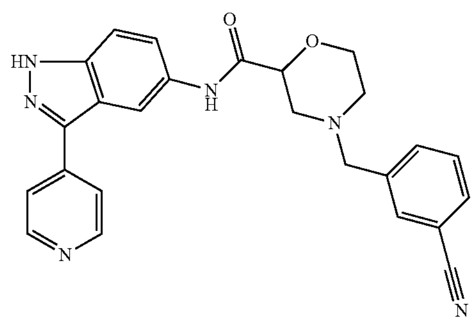 [SMILES: N#Cc1cccc(CN2CCOC(C(=O)Nc3ccc4[nH]nc(-c5ccncc5)c4c3)C2)c1] | 4-[(3-CYANOPHENYL)METHYL]-N-[3-(4-PYRIDINYL)-1H-INDAZOL-5-YL]-2-MORPHOLINE-CARBOXAMIDE | 2723 | 1178.5 | | 438.2 | 439.1 | 2.164 |
| 32 | 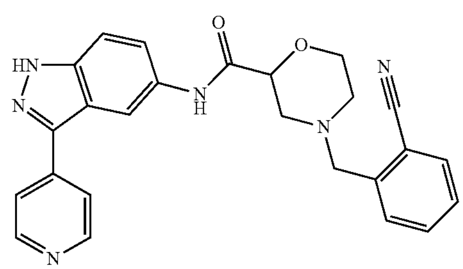 [SMILES: N#Cc1ccccc1CN1CCOC(C(=O)Nc2ccc3[nH]nc(-c4ccncc4)c3c2)C1] | 4-[(2-CYANOPHENYL)METHYL]-N-[3-(4-PYRIDINYL)-1H-INDAZOL-5-YL]-2-MORPHOLINE-CARBOXAMIDE | 775 | 382.8 | | 438.2 | 439.1 | 2.379 |
| 33 | 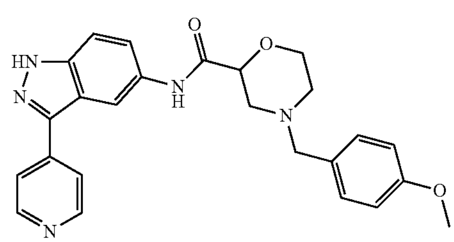 | 4-[(4-METHOXYPHENYL)METHYL]-N-[3-(4-PYRIDINYL)-1H-INDAZOL-5-YL]-2-MORPHOLINE-CARBOXAMIDE | 1142 | 225.6 | | 443.2 | 444.1 | 2.32 |

-continued

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 34 | 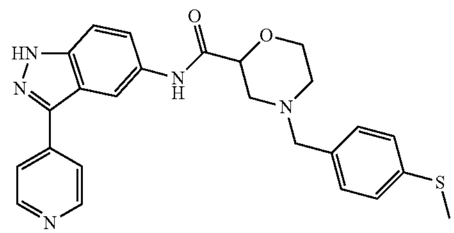 [SMILES: COc1ccc(CN2CCOC(C(=O)Nc3ccc4[nH]nc(-c5ccncc5)c4c3)C2)cc1] | 4-[[4-(METHYLTHIO)PHENYL]METHYL]-N-[3-(4-PYRIDINYL)-1H-INDAZOL-5-YL]-2-MORPHOLINE-CARBOXAMIDE | 423 | 508.2 | 956.6 | 459.2 | 460.1 | 2.581 |
| 35 | 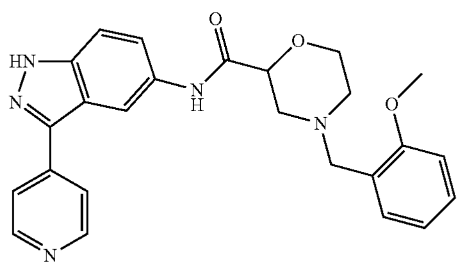 [SMILES: COc1ccccc1CN1CCOC(C(=O)Nc2ccc3[nH]nc(-c4ccncc4)c3c2)C1] | 4-[(2-METHOXYPHENYL)METHYL]-N-[3-(4-PYRIDINYL)-1H-INDAZOL-5-YL]-2-MORPHOLINE-CARBOXAMIDE | 79 | 80.9 | 37.9 | 443.2 | 444.1 | 2.365 |
| 36 | 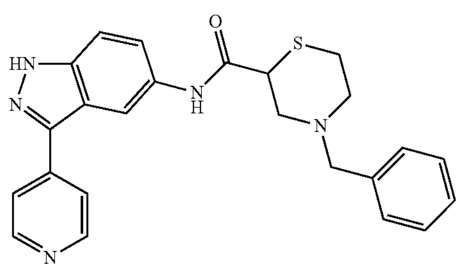 [SMILES: O=C(Nc1ccc2[nH]nc(-c3ccncc3)c2c1)C1CN(Cc2ccccc2)CCS1] | 4-(PHENYLMETHYL)-N-[3-(4-PYRIDINYL)-1H-INDAZOL-5-YL]-2-THIOMORPHOLINE-CARBOXAMIDE | 62 | 165.7 | 1840.5 | 429.2 | 430.1 | 2.341 |
| 37 | 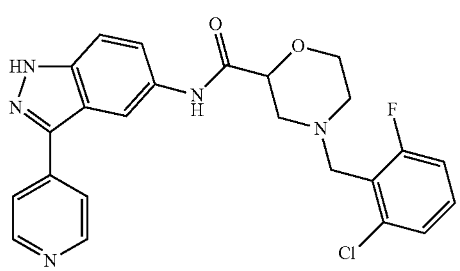 [SMILES: O=C(Nc1ccc2[nH]nc(-c3ccncc3)c2c1)C1CN(Cc2c(F)cccc2Cl)CCO1] | 4-[(2-CHLORO-6-FLUOROPHENYL)METHYL]-N-[3-(4-PYRIDINYL)-1H-INDAZOL-5-YL]-2-MORPHOLINE-CARBOXAMIDE | 27 | 173.3 | 110.6 | 465.1 | 466.1 | 1.788 |
| 38 | 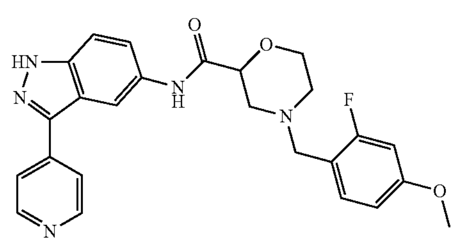 [SMILES: COc1ccc(CN2CCOC(C(=O)Nc3ccc4[nH]nc(-c5ccncc5)c4c3)C2)c(F)c1] | 4-[(2-FLUORO-4-METHOXYPHENYL)METHYL]-N-[3-(4-PYRIDINYL)-1H-INDAZOL-5-YL]-2-MORPHOLINE-CARBOXAMIDE | 588 | 556.2 | | 461.2 | 462.3 | 1.77 |

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 39 | 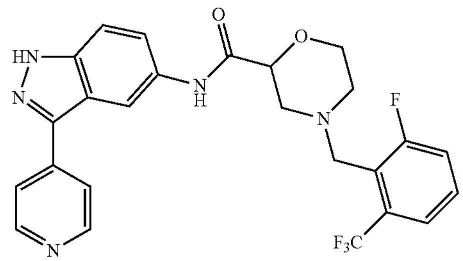 [SMILES: O=C(Nc1ccc2[nH]nc(-c3ccncc3)c2c1)C1CN(Cc2c(F)cccc2C(F)(F)F)CCO1] | 4-[[2-FLUORO-6-(TRIFLUORO-METHYL) PHENYL]METHYL]-N-[3-(4-PYRIDINYL)-1H-INDAZOL-5-YL]-2-MORPHOLINE-CARBOXAMIDE | 715 | 4760.7 | | 499.2 | 500.2 | 2.029 |
| 40 | 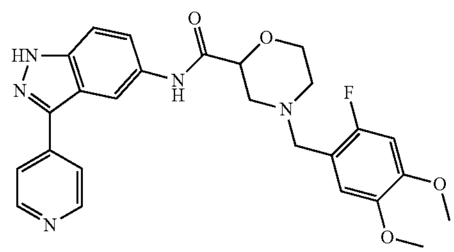 [SMILES: COc1cc(F)c(CN2CCOC(C(=O)Nc3ccc4[nH]nc(-c5ccncc5)c4c3)C2)cc1OC] | 4-[(2-FLUORO-4,5-DIMETHOXY-PHENYL) METHYL]-N-[3-(4-PYRIDINYL)-1H-INDAZOL-5-YL]-2-MORPHOLINE-CARBOXAMIDE | 1186 | 1107.9 | | 491.2 | 492.3 | 1.747 |
| 41 | 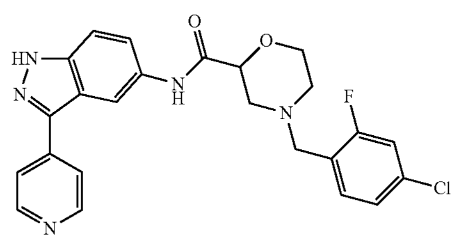 [SMILES: O=C(Nc1ccc2[nH]nc(-c3ccncc3)c2c1)C1CN(Cc2ccc(Cl)cc2F)CCO1] | 4-[(4-CHLORO-2-FLUOROPHENYL) METHYL]-N-[3-(4-PYRIDINYL)-1H-INDAZOL-5-YL]-2-MORPHOLINE-CARBOXAMIDE | 584 | 419.1 | | 465.1 | 466.1 | 1.893 |
| 42 | 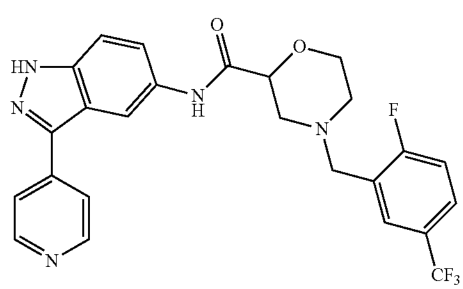 [SMILES: O=C(Nc1ccc2[nH]nc(-c3ccncc3)c2c1)C1CN(Cc2cc(C(F)(F)F)ccc2F)CCO1] | 4-[[2-FLUORO-5-(TRIFLUORO-METHYL) PHENYL]METHYL]-N-[3-(4-PYRIDINYL)-1H-INDAZOL-5-YL]-2-MORPHOLINE-CARBOXAMIDE | 1263 | 2662.2 | | 499.2 | 500.2 | 2.006 |
| 43 | 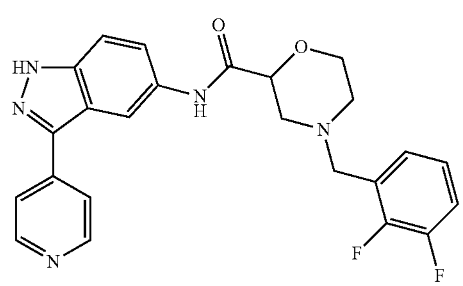 [SMILES: O=C(Nc1ccc2[nH]nc(-c3ccncc3)c2c1)C1CN(Cc2cccc(F)c2F)CCO1] | 4-[(2,3-DIFLUOROPHENYL) METHYL]-N-[3-(4-PYRIDINYL)-1H-INDAZOL-5-YL]-2-MORPHOLINE-CARBOXAMIDE | 214 | 217.8 | 139.3 | 449.2 | 450.2 | 1.719 |

-continued

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 44 | 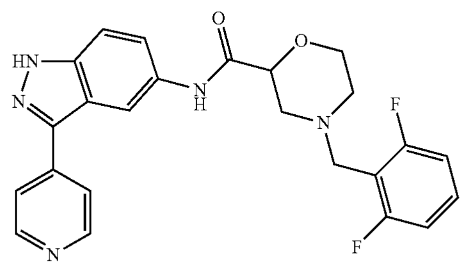 [SMILES: O=C(Nc1ccc2[nH]nc(-c3ccncc3)c2c1)C1CN(Cc2c(F)cccc2F)CCO1] | 4-[(2,6-DIFLUOROPHENYL)METHYL]-N-[3-(4-PYRIDINYL)-1H-INDAZOL-5-YL]-2-MORPHOLINE-CARBOXAMIDE | 165 | 108.6 | 69.2 | 449.2 | 450.2 | 1.65 |
| 45 | 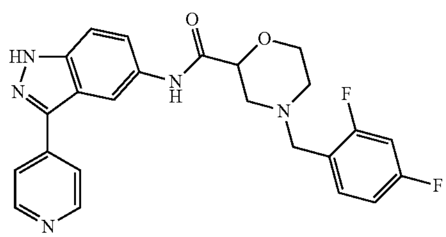 [SMILES: O=C(Nc1ccc2[nH]nc(-c3ccncc3)c2c1)C1CN(Cc2ccc(F)cc2F)CCO1] | 4-[(2,4-DIFLUOROPHENYL)METHYL]-N-[3-(4-PYRIDINYL)-1H-INDAZOL-5-YL]-2-MORPHOLINE-CARBOXAMIDE | 80 | 274.6 | 138.0 | 449.2 | 450.2 | 1.678 |
| 46 | 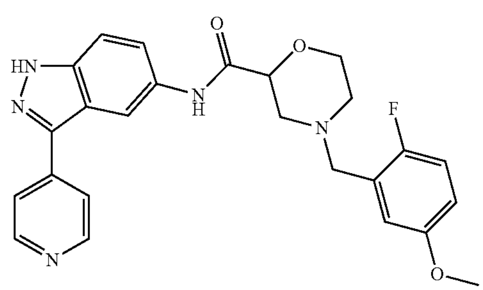 [SMILES: COc1ccc(F)c(CN2CCOC(C(=O)Nc3ccc4[nH]nc(-c5ccncc5)c4c3)C2)c1] | 4-[(2-FLUORO-5-METHOXYPHENYL)METHYL]-N-[3-(4-PYRIDINYL)-1H-INDAZOL-5-YL]-2-MORPHOLINE-CARBOXAMIDE | 167 | 148.2 | 148.4 | 461.2 | 462.2 | 1.765 |
| 47 | 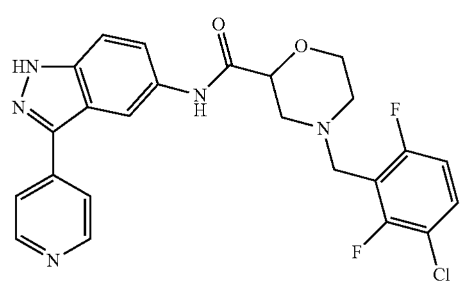 [SMILES: O=C(Nc1ccc2[nH]nc(-c3ccncc3)c2c1)C1CN(Cc2c(F)ccc(Cl)c2F)CCO1] | 4-[(3-CHLORO-2,6-DIFLUOROPHENYL)METHYL]-N-[3-(4-PYRIDINYL)-1H-INDAZOL-5-YL]-2-MORPHOLINE-CARBOXAMIDE | 223 | 452.0 | 581.2 | 483.1 | 484.1 | 1.96 |
| 48 | 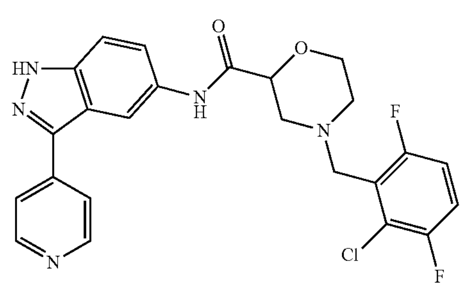 [SMILES: O=C(Nc1ccc2[nH]nc(-c3ccncc3)c2c1)C1CN(Cc2c(F)ccc(F)c2Cl)CCO1] | 4-[(2-CHLORO-3,6-DIFLUOROPHENYL)METHYL]-N-[3-(4-PYRIDINYL)-1H-INDAZOL-5-YL]-2-MORPHOLINE-CARBOXAMIDE | 202 | 908.6 | 370.9 | 483.1 | 484.1 | 1.91 |

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 49 | 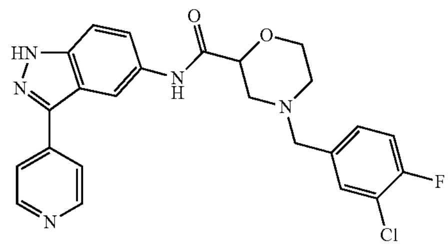 [SMILES: O=C(Nc1ccc2[nH]nc(-c3ccncc3)c2c1)C1CN(Cc2ccc(F)c(Cl)c2)CCO1] | 4-[(3-CHLORO-4-FLUOROPHENYL)METHYL]-N-[3-(4-PYRIDINYL)-1H-INDAZOL-5-YL]-2-MORPHOLINE-CARBOXAMIDE | 910 | 1784.2 | | 465.1 | 466.1 | 1.895 |
| 50 | 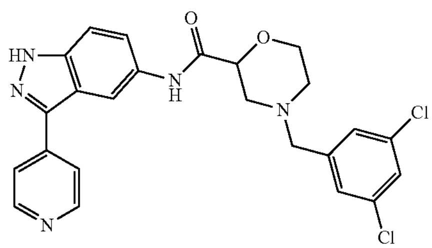 [SMILES: O=C(Nc1ccc2[nH]nc(-c3ccncc3)c2c1)C1CN(Cc2cc(Cl)cc(Cl)c2)CCO1] | 4-[(3,5-DICHLOROPHENYL)METHYL]-N-[3-(4-PYRIDINYL)-1H-INDAZOL-5-YL]-2-MORPHOLINE-CARBOXAMIDE | 500 | 8844.2 | 8677.1 | 481.1 | 482.1 | 2.28 |
| 51 | 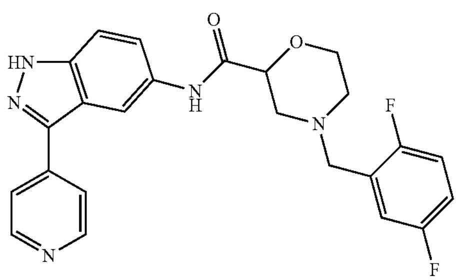 [SMILES: O=C(Nc1ccc2[nH]nc(-c3ccncc3)c2c1)C1CN(Cc2cc(F)ccc2F)CCO1] | 4-[(2,5-DIFLUOROPHENYL)METHYL]-N-[3-(4-PYRIDINYL)-1H-INDAZOL-5-YL]-2-MORPHOLINE-CARBOXAMIDE | 727 | 399.5 | | 449.2 | 450.29 | 2.17 |
| 52 | 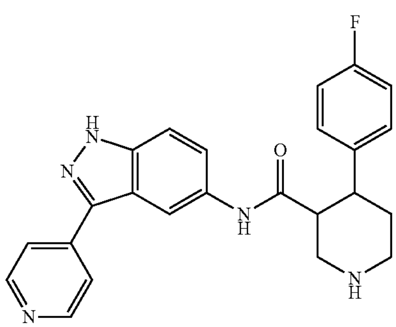 [SMILES: O=C(Nc1ccc2[nH]nc(-c3ccncc3)c2c1)C1CNCCC1c1ccc(F)cc1] | 4-(4-FLUOROPHENYL)-N-(3-(PYRIDIN-4-YL)-1H-INDAZOL-5-YL)PIPERIDINE-3-CARBOXAMIDE | 18 | 60.8 | 56.5 | 415.2 | 416.19 | 2.24 |
| 53 | 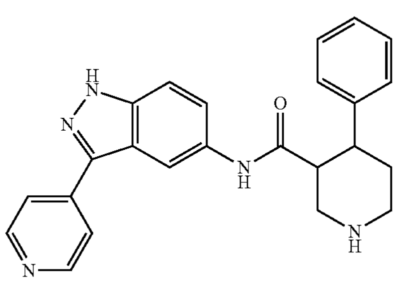 [SMILES: O=C(Nc1ccc2[nH]nc(-c3ccncc3)c2c1)C1CNCCC1c1ccccc1] | 4-PHENYL-N-[3-(4-PYRIDINYL)-1H-INDAZOL-5-YL]-3-PIPERIDINE-CARBOXAMIDE | 70 | 69.5 | 102.4 | 397.2 | 398.32 | 2.16 |

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 54 | 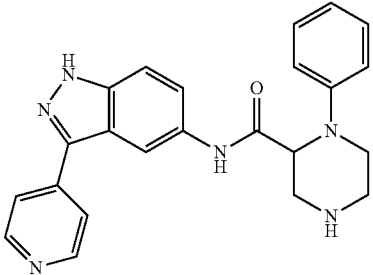 [SMILES: O=C(Nc1ccc2[nH]nc(-c3ccncc3)c2c1)C1CNCCN1c1ccccc1] | 1-PHENYL-N-[3-(4-PYRIDINYL)-1H-INDAZOL-5-YL]-2-PIPERAZINE-CARBOXAMIDE | 30 | 168.5 | | 398.2 | 399.35 | 2.37 |
| 55 | 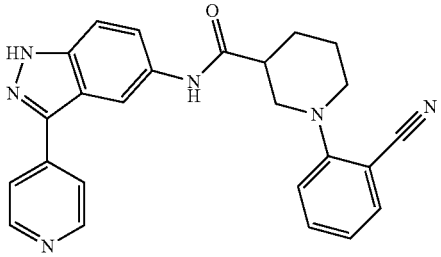 [SMILES: N#Cc1ccccc1N1CCCC(C(=O)Nc2ccc3[nH]nc(-c4ccncc4)c3c2)C1] | 1-(2-CYANOPHENYL)-N-[3-(4-PYRIDINYL)-1H-INDAZOL-5-YL]-3-PIPERIDINE-CARBOXAMIDE | 23 | 91.5 | 82.3 | 422.2 | 423.34 | 3.36 |
| 56 | 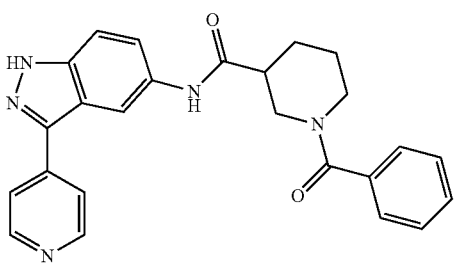 [SMILES: O=C(Nc1ccc2[nH]nc(-c3ccncc3)c2c1)C1CCCN(C(=O)c2ccccc2)C1] | 1-BENZOYL-N-[3-(4-PYRIDINYL)-1H-INDAZOL-5-YL]-3-PIPERIDINE-CARBOXAMIDE | 420 | 149.8 | 553.4 | 425.2 | 426.1 | 2.998 |
| 57 | 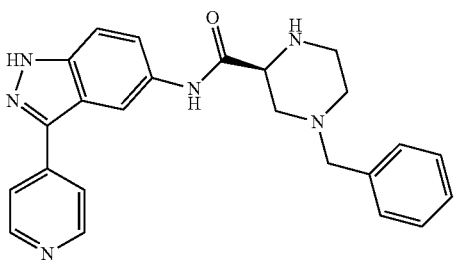 [SMILES: O=C(Nc1ccc2[nH]nc(-c3ccncc3)c2c1)[C@@H]1CN(Cc2ccccc2)CCN1] | 4-(PHENYLMETHYL)-N-[3-(4-PYRIDINYL)-1H-INDAZOL-5-YL]-2(S)-PIPERAZINE-CARBOXAMIDE | 49 | 61.8 | 52.0 | 412.2 | 413.2 | 2.315 |
| 58 | 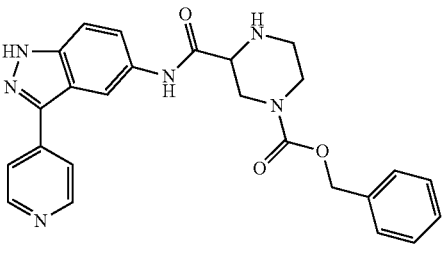 [SMILES: O=C(Nc1ccc2[nH]nc(-c3ccncc3)c2c1)C1CN(C(=O)OCc2ccccc2)CCN1] | PHENYLMETHYL 3-[[[3-(4-PYRIDINYL)-1H-INDAZOL-5-YL]AMINO]CARBONYL]-1-PIPERAZINE-CARBOXYLATE | 602 | 960.5 | 2197.0 | 456.2 | 457.19 | 2.37 |

-continued

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 59 | 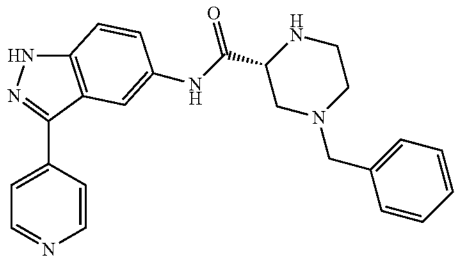 [SMILES: O=C(Nc1ccc2[nH]nc(-c3ccncc3)c2c1)[C@H]1CN(Cc2ccccc2)CCN1] | 4-(PHENYLMETHYL)-N-[3-(4-PYRIDINYL)-1H-INDAZOL-5-YL]-2(R)-PIPERAZINE-CARBOXAMIDE | 21 | 21.6 | 16.3 | 412.2 | 413.1 | 2.325 |
| 60 | 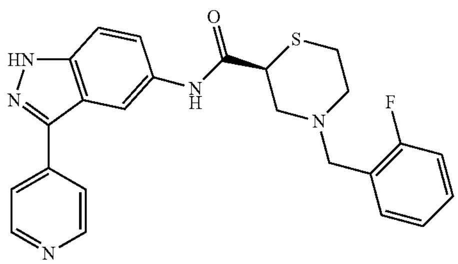 [SMILES: O=C(Nc1ccc2[nH]nc(-c3ccncc3)c2c1)[C@@H]1CN(Cc2ccccc2F)CCS1] | 4-[(2-FLUOROPHENYL)METHYL]-N-[3-(4-PYRIDINYL)-1H-INDAZOL-5-YL]-2(S)-THIOMORPHOLINE-CARBOXAMIDE | 6 | 72.3 | 174.5 | 447.2 | 448.31 | 2.18 |
| 61 | 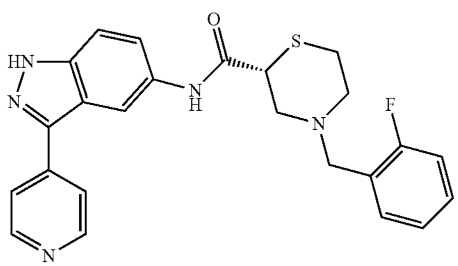 [SMILES: O=C(Nc1ccc2[nH]nc(-c3ccncc3)c2c1)[C@H]1CN(Cc2ccccc2F)CCS1] | 4-[(2-FLUOROPHENYL)METHYL]-N-[3-(4-PYRIDINYL)-1H-INDAZOL-5-YL]-2(R)-THIOMORPHOLINE-CARBOXAMIDE | 5 | 19.9 | 8.1 | 447.2 | 448.31 | 2.18 |
| 62 | 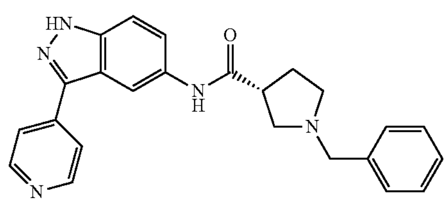 [SMILES: O=C(Nc1ccc2[nH]nc(-c3ccncc3)c2c1)[C@@H]1CCN(Cc2ccccc2)C1] | 1-(PHENYLMETHYL)-N-[3-(4-PYRIDINYL)-1H-INDAZOL-5-YL]-3(R)-PYRROLIDINE-CARBOXAMIDE | 34.5 | | 287.1 | 397.2 | 398.67 | 1.92 |
| 63 | 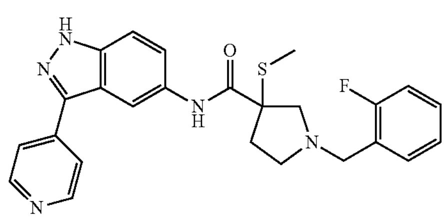 [SMILES: CSC1(C(=O)Nc2ccc3[nH]nc(-c4ccncc4)c3c2)CCN(Cc2ccccc2F)C1] | 1-[(2-FLUOROPHENYL)METHYL]-3-(METHYLTHIO)-N-[3-(4-PYRIDINYL)-1H-INDAZOL-5-YL]-3-PYRROLIDINE-CARBOXAMIDE | 13.5 | 120.9 | 211.1 | 461.2 | 462.56 | 2.17 |
| 64 | 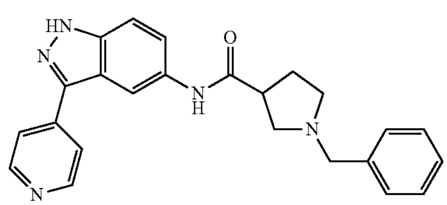 [SMILES: O=C(Nc1ccc2[nH]nc(-c3ccncc3)c2c1)C1CCN(Cc2ccccc2)C1] | 1-(PHENYLMETHYL)-N-[3-(4-PYRIDINYL)-1H-INDAZOL-5-YL]-3-PYRROLIDINE-CARBOXAMIDE | 35.6 | 170.6 | 244.9 | 397.2 | 398.62 | 2.03 |

-continued

| Compd # | Structure | Chemical Names | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 65 | 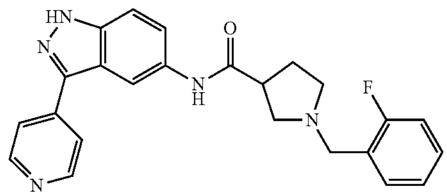 [SMILES: O=C(Nc1ccc2[nH]nc(-c3ccncc3)c2c1)C1CCN(Cc2ccccc2F)C1] | 1-[(2-FLUOROPHENYL)METHYL]-N-[3-(4-PYRIDINYL)-1H-INDAZOL-5-YL]-3-PYRROLIDINE-CARBOXAMIDE | 29.4 | 77.1 | 100.4 | 415.2 | 416.60 | 2.03 |
| 66 | 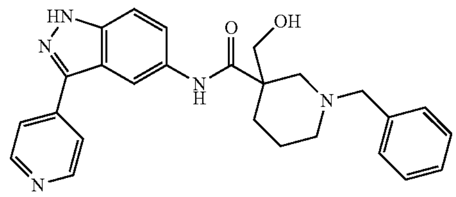 [SMILES: O=C(Nc1ccc2[nH]nc(-c3ccncc3)c2c1)C1(CO)CCCN(Cc2ccccc2)C1] | 3-(HYDROXYMETHYL)-1-(PHENYLMETHYL)-N-[3-(4-PYRIDINYL)-1H-INDAZOL-5-YL]-3-PIPERIDINE-CARBOXAMIDE | 104 | 1000.0 | 439.0 | 441.2 | 442.65 | 2.02 |
| 67 | 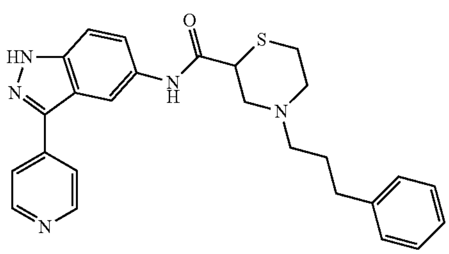 [SMILES: O=C(Nc1ccc2[nH]nc(-c3ccncc3)c2c1)C1CN(CCCc2ccccc2)CCS1] | 4-(3-PHENYLPROPYL)-N-[3-(4-PYRIDINYL)-1H-INDAZOL-5-YL]-2-THIOMORPHOLINE-CARBOXAMIDE | | | 1000 | 457.2 | 458.65 | 2.43 |
| 68 | 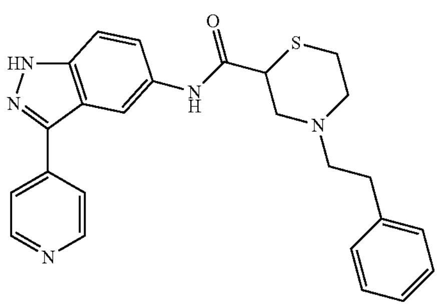 [SMILES: O=C(Nc1ccc2[nH]nc(-c3ccncc3)c2c1)C1CN(CCc2ccccc2)CCS1] | 4-(2-PHENYLETHYL)-N-[3-(4-PYRIDINYL)-1H-INDAZOL-5-YL]-2-THIOMORPHOLINE-CARBOXAMIDE | | | 895 | 443.2 | 444.61 | 2.21 |

4-(2-Fluorobenzyl)-N-(3-(pyridin-4-yl)-1H-indazol-5-yl)thiomorpholine-1-oxide-2-carboxamide

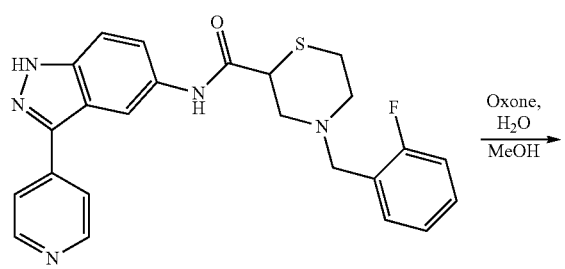

-continued

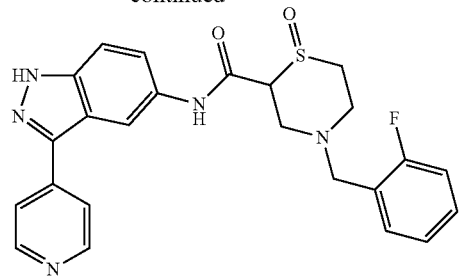

In a flask, methanol (0.1788 mL) was added to 4-(2-fluorobenzyl)-N-(3-(pyridin-4-yl)-1H-indazol-5-yl)thiomorpholine-2-carboxamide (0.02 g, 0.0447 mmol). The reaction was cooled to 0° C. At 0° C., oxone (0.078 mL, 0.75M in $H_2O$) was added, and the reaction was stirred for 5 minutes at 0° C. The reaction was quenched using sodium sulfite and water until the reaction turns clear. The crude was extracted using dichloromethane (3×1 mL). The extracts were combined and washed with water then brine, and further it was dried using anhydrous sodium sulfate. The mixture was purified using prep LC/MS. LC-MS: 464.0 [M+H]. LC/MS RT=2.155 min and 2.409 min.

4-(2-Fluorobenzyl)-N-(3-(pyridin-4-yl)-1H-indazol-5-yl)thiomorpholine-1,1-dioxide-2-carboxamide

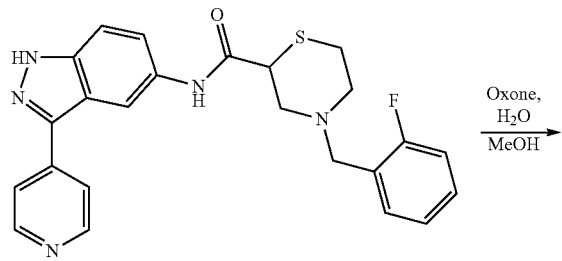

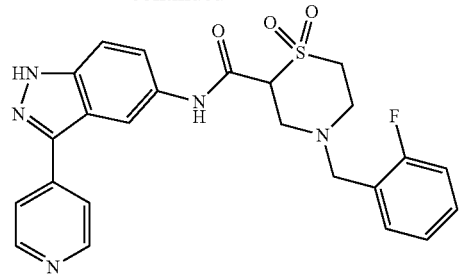

In a flask, methanol (0.1788 mL) was added to 4-(2-fluoroberizyl)-N-(3-(pyridin-4-yl)-1H-indazol-5-yl)thiomorpholine-2-carboxamide (0.02 g, 0.0447 mmol). The reaction was cooled to 0° C. At 0° C., oxone (0.078 mL, 0.75M in H$_2$O) was added, and the reaction was stirred for 5 minutes at 0° C. The reaction was quenched using sodium sulfite and water until the reaction turns clear. The crude was extracted using dichloromethane (3×1 mL). The extracts were combined and washed with water then brine, and further it was dried using anhydrous sodium sulfate. The mixture was purified using prep LC/MS. LC-MS: 480.1 [M+H]. LC/MS RT=3.036 min.

| Compound # | Structure | Chemical Name | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 69 | 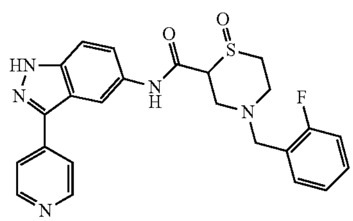 [SMILES: O=C(Nc1ccc2[nH]nc(-c3ccncc3)c2c1)C1CN(Cc2ccccc2F)CCS1=O] | 4-[(2-FLUOROPHENYL)METHYL]-N-[3-(4-PYRIDINYL)-1H-INDAZOL-5-YL]-2-THIOMORPHOLINECARBOXAMIDE, 1-OXIDE | 4.4 | 8.3 | 2.7 | 463.1 | 464 | 2.155, 2.409 |
| 70 | 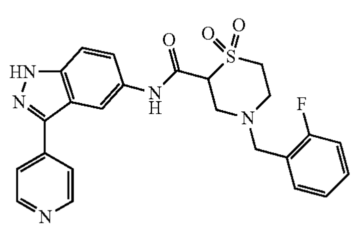 [SMILES: O=C(Nc1ccc2[nH]nc(-c3ccncc3)c2c1)C1CN(Cc2ccccc2F)CCS1(=O)=O] | 4-[(2-FLUOROPHENYL)METHYL]-N-[3-(4-PYRIDINYL)-1H-INDAZOL-5-YL]-2-THIOMORPHOLINECARBOXAMIDE, 1,1-DIOXIDE | 12 | 17.7 | 13.9 | 479.1 | 480.1 | 3.036 |

(3S)-tert-butyl 1-(1-phenylethyl)piperidine-3-carboxylate

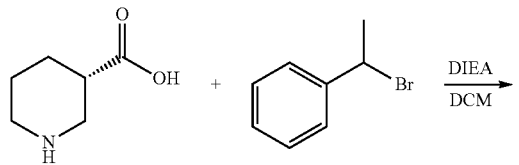

In a flask, dichloromethane (0.432 mL) was added to (S)-tert-butyl piperidine-3-carboxylate (0.020 g, 0.108 mmol). At 0° C., (1-bromoethyl)benzene (0.030 g, 0.162 mmol) was added to the reaction. The solution was allowed to stir from 0° C. to room temperature for 3 hrs. The reaction was quenched using water (1 mL) and extracted using dichloromethane (3×1 mL). The extractions were combined and dried using sodium sulfate. The extracts were concentrated in vacuo, and the crude product was progressed to the next step without further purification.

(3S)-1-(1-phenylethyl)piperidine-3-carboxylic acid

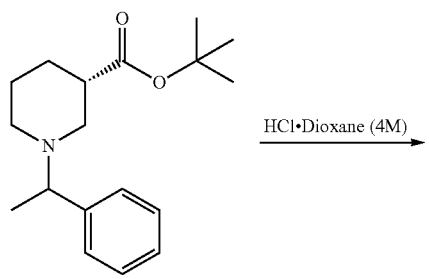

In a flask, hydrochloric acid in dioxane (4M, 2 mL) was added to (3S)-tert-butyl 1-(1-phenylethyl)piperidine-3-carboxylate (0.031 g, 0.108 mmol), and the reaction was stirred for 30 minutes. Ethanol (2 mL) was added to the reaction, and the resulting solution was concentrated in vacuo. The crude product was progressed to the next step without further purification.

Ethyl 8-benzyl-1,4-dioxa-8-azaspiro[4.5]decane-6-carboxylate

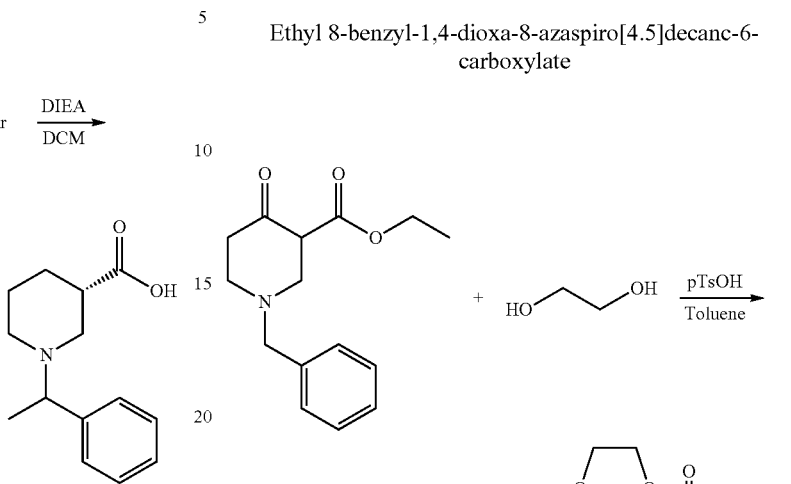

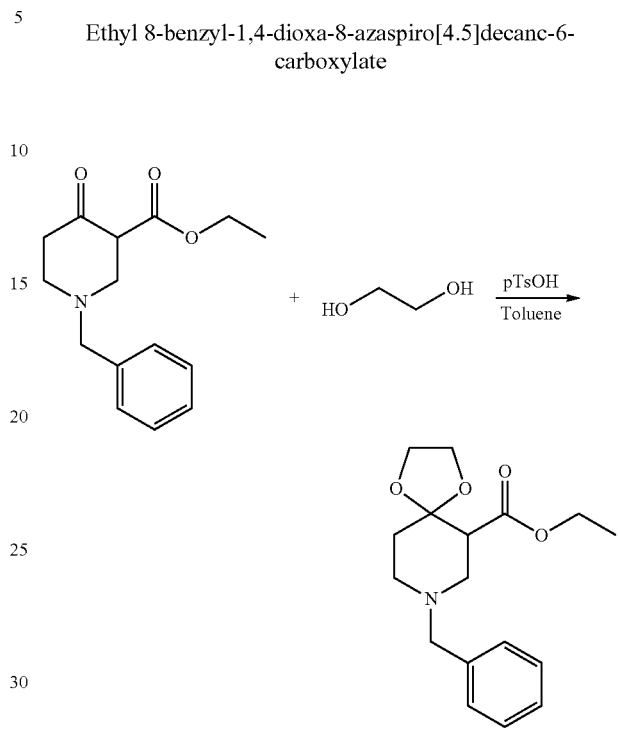

Toluene was added to a flask containing ethyl 1-benzyl-4-oxopiperidine-3-carboxylate (0.100 g, 0.340 mmol) and p-toluenesulfonic acid (0.0032 g, 0.017 mmol). Ethane-1,2-diol (0.042 g, 0.67 mmol) was added to the mixture. The reaction was stirred for 18 hr at reflux with a Dean-Stark attachment. The reaction was concentrated in vacuo, and the crude product was progressed to the next step without further purification.

8-Benzyl-1,4-dioxa-8-azaspiro[4.5]decane-6-carboxylic acid

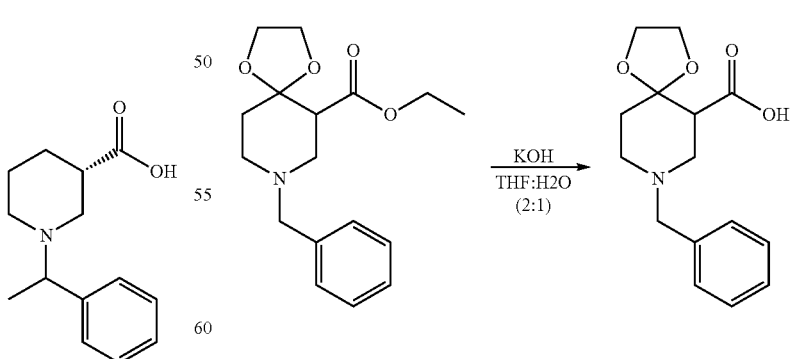

In a flask, etrahydrofuran (0.890 mL) was added to ethyl 8-benzyl-1,4-dioxa-8-azaspiro[4.5]decane-6-carboxylate (0.0813 g, 0.267 mmol). Potassium hydroxide (0.2157 g, 3.9 mmol) in water (0.445 mL) was added to the solution, and the reaction was allowed to stir for 3 hrs at 40° C. The reaction was neutralized to pH 7 using 1N hydrochloric acid. The reaction was concentrated under vacuo and purified using prep LC/MS. LC-MS: 278.65 [M+H]. LC/MS RT=1.66 min.

1-Tert-butyl 3-methyl 4-hydroxypiperidine-1,3-dicarboxylate

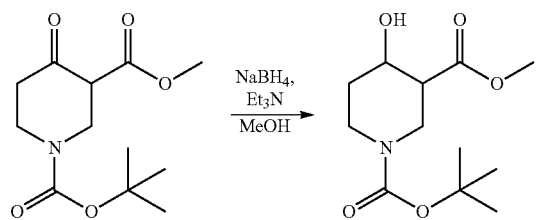

In a flask, methanol (1.425 mL) and triethylamine (0.0277 g, 0.274 mmol) was added to 1-tert-butyl 3-methyl 4-oxopiperidine-1,3-dicarboxylate (0.0587 g, 0.228 mmol). The reaction was allowed to stir at room temperature for 15 minutes. Sodium borohydride (0.0285 g, 0.753 mmol) was added to the flask one portion. The reaction was allowed to stir at room temperature for an additional hour. Using 1N hydrochloric acid, the reaction was neutralized to pH 7 and then concentrated under vacuo. Water (2 mL) was used to dissolve the residue. The mixture was extracted using dichloromethane (3×2 mL). The extracts were combined, washed with saturated sodium bicarbonate, dried using sodium sulfate, and concentrated under vacuo. The crude product was progressed to the next step without further purification.

1-(tert-butoxycarbonyl)-4-hydroxypiperidine-3-carboxylic acid

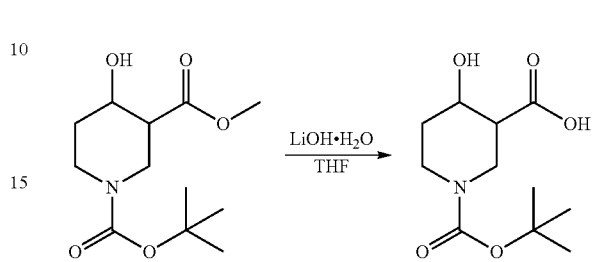

In a flask, tetrahydrofuran (1.01 mL) was added to 1-tert-butyl 3-methyl 4-hydroxypiperidine-1,3-dicarboxylate (0.079 g, 0.303 mmol). A solution of lithium hydroxide (0.0254 g, 0.607 mmol) in water (0.505 mL) was added to the reaction. The reaction was allowed to stir at room temperature for 4 hrs. Using 1N hydrochloric acid, the reaction was neutralized to pH 6 and was concentrated in vacuo. The crude product was purified using prep LC/MS. LC-MS: 190.1 [M–t-butyl]. LC/MS RT=2.58 min.

| Compd # | Structure | Chemical Name | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 71 | 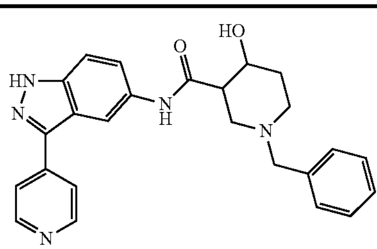 | 4-HYDROXY-1-(PHENYLMETHYL)-N-[3-(4-PYRIDINYL)-1H-INDAZOL-5-YL]-3-PIPERIDINECARBOXAMIDE | 84.1 | | | 427.2 | 428.2 | 1.543 |
| 72 | 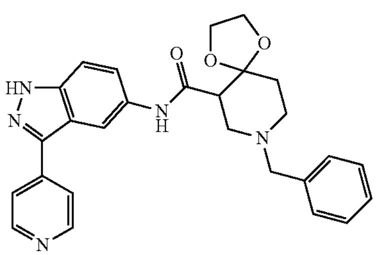 [SMILES: O=C(Nc1ccc2[nH]nc(-c3ccncc3)c2c1)C1CN(Cc2ccccc2)CCC12OCCO2] | 8-(PHENYLMETHYL)-N-[3-(4-PYRIDINYL)-1H-INDAZOL-5-YL]-1,4-DIOXA-8-AZASPIRO[4.5]DECANE-6-CARBOXAMIDE | 221.7 | 1000.0 | | 469.2 | 470.64 | 2.14 |
| 73 | 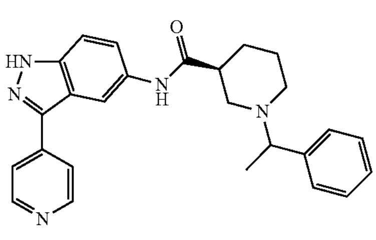 [SMILES: CC(c1ccccc1)N1CCC[C@H](C(=O)Nc2ccc3[nH]nc(-c4ccncc4)c3c2)C1] | 1-(1-PHENYLETHYL)-N-[3-(4-PYRIDINYL)-1H-INDAZOL-5-YL]-3(S)-PIPERIDINECARBOXAMIDE, | 25.9 | 192.5 | | 425.2 | 426.65 | 2.22 |

-continued
| Compd # | Structure | Chemical Name | TdF Kd (nM) | cERK2 IC50 (nM) | aERK2 IC50 (nM) | Calc. Mass | Obs. M + H | Retention time 10 min method (min.) |
|---|---|---|---|---|---|---|---|---|
| 74 | 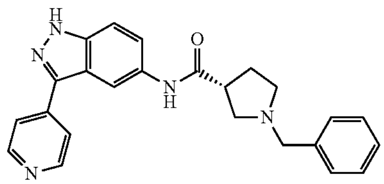 [SMILES: O=C(Nc1ccc2[nH]nc(-c3ccncc3)c2c1)[C@@H]1CCN(Cc2ccccc2)C1] | 1-(PHENYLMETHYL)-N-[3-(4-PYRIDINYL)-1H-INDAZOL-5-YL]-3(R)-PYRROLIDINE-CARBOXAMIDE | 34.5 | | 287.1 | 397.2 | 398.67 | 1.92 |
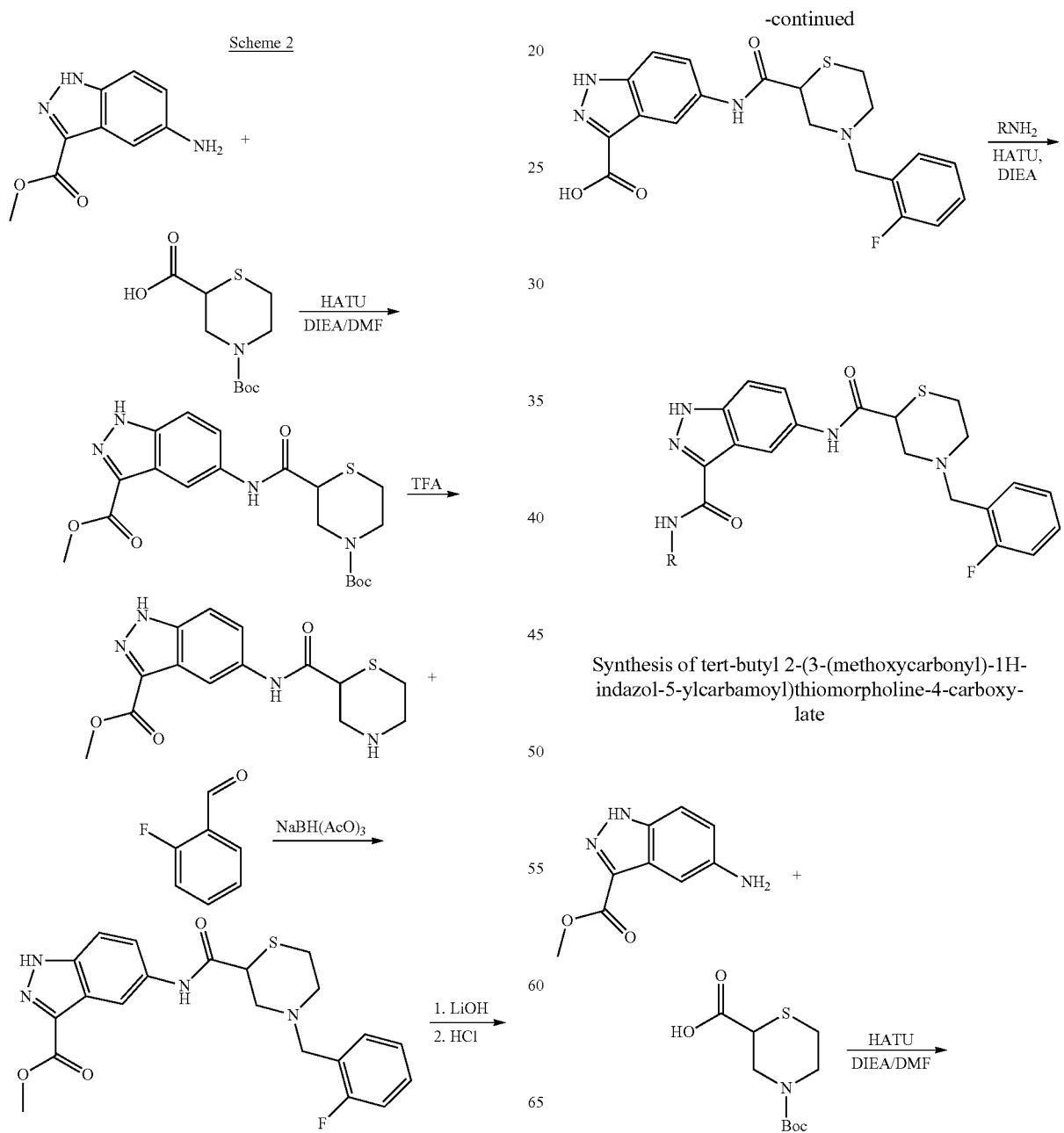
Synthesis of tert-butyl 2-(3-(methoxycarbonyl)-1H-indazol-5-ylcarbamoyl)thiomorpholine-4-carboxylate

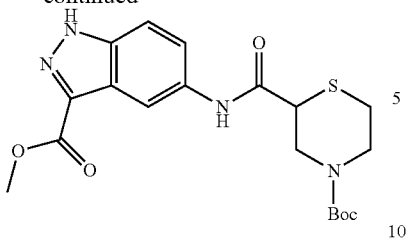

2-(7-Aza-1H-benzotriazole-1-yl)-1,1,3,3-tetramethyluronium hexafluorophosphate (HATU) (1.9 g, 5 mmol) and diisopropyl ethyl amine (DIEA) (2.7 mL) was added to a suspension of 4-(tert-butoxycarbonyl)thiomorpholine-2-carboxylic acid (1.3 g, 5 mmol) in DMF (10 mL) and was stirred at room temperature for 15 minutes. Methyl 5-amino-1H-indazole-3-carboxylate (0.95 g, 5 mmol)) was added to the reaction and was stirred at room temperature for an additional 30 minutes. The reaction was quenched with water (50 mL) and extracted with ethyl acetate (3×20 mL). The extracts were combined, dried using anhydrous sodium sulfate, filtered, and concentrated in vacuo. The crude product (2.1 g) was progressed to the next step without purification.

Synthesis of methyl 5-(thiomorpholine-2-carboxamido)-1H-indazole-3-carboxylate

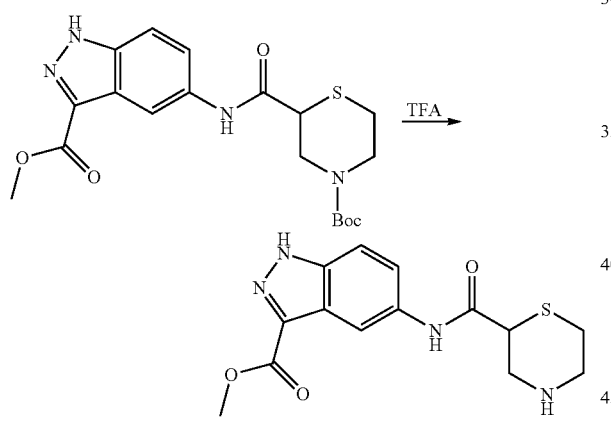

Trifluoroacetic acid (10 mL) and dichloromethane (5 mL) was added to tert-butyl 2-(3-(methoxycarbonyl)-1H-indazol-5-ylcarbamoyl) thiomorpholine-4-carboxylate (2.1 g, 5 mmol) and was stirred at room temperature for 30 minutes. The reaction was concentrated in vacuo, and the crude product was progress to the next step without further purification.

Synthesis of methyl 5-(4-(2-fluorobenzyl)thiomorpholine-2-carboxamido)-1H-indazole-3-carboxylate

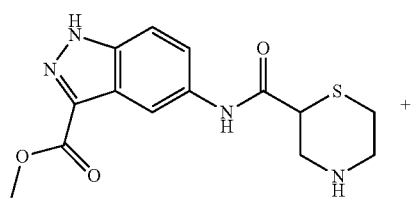

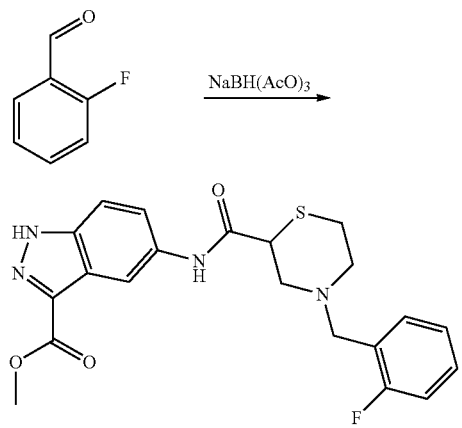

In a flask, dichloromethane (5 mL) and acetic acid (3 drops) was added to methyl 5-(thiomorpholine-2-carboxamido)-1H-indazole-3-carboxylate (0.320 g, 1 mmol) and 2-fluorobenzaldehyde (0.248 g, 2 mmol). The reaction was stirred for 15 minutes. Sodium triacetoxyborohydride (0.636 g, 3 mmol) was added in one portion. The reaction was stirred for an additional 16 hours. Saturated sodium bicarbarbonate (20 mL) was added. The reaction was stirred for an additional 5 minutes and was extracted with dichloromethane (30×1 mL). The extracts were combined, dried with anhydrous sodium sulfate, filtered, and concentrated in vacuo. The resulting crude product was purified by flash column chromatography to give 250 mg product. LC-MS: 429.1.2 [M+H].

Synthesis of 5-(4-(2-fluorobenzyl)thiomorpholine-2-carboxamido)-1H-indazole-3-carboxylic acid

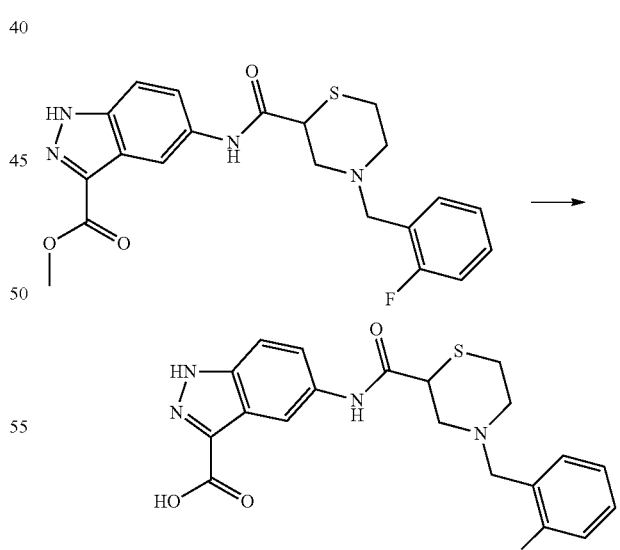

To a solution of methyl 5-(4-(2-fluorobenzyl)thiomorpholine-2-carboxamido)-1H-indazole-3-carboxylate (250 mg, 0.58 mmol) in THF (4 mL), was added LiOH (1.2 mL, 1M, 1.2 mmol). The resulted solution was stirred at RT for overnight. 1 N HCl was added to the reaction mixture until pH reached around 4. The solvent was removed and the residual was used directly for the next step. LC-MS: 415.1 [M+H]

Synthesis of 4-(2-fluorobenzyl)-N-(3-(methylcarbamoyl)-1H-indazol-5-yl)thiomorpholine-2-carboxamide

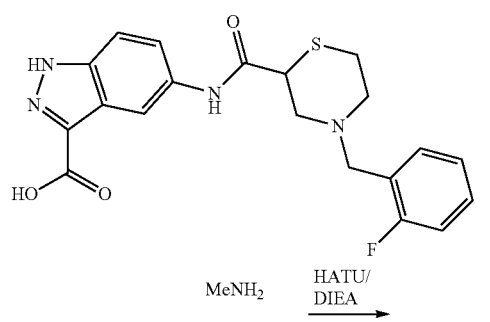

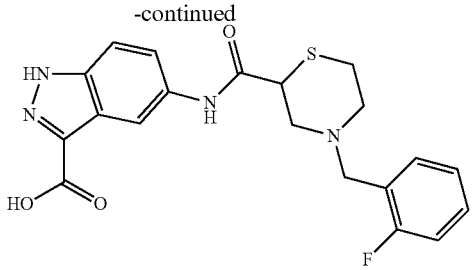

To a solution of 5-(4-(2-fluorobenzyl)thiomorpholine-2-carboxamido)-1H-indazole-3-carboxylic acid (41 mg, 0.1 mmol) and DIEA (35 µL) in DMF was added HATU (38 mg, 0.1 mmol). The resulted solution was stirred for 10 min before methyl amine hydrochloride (13 mg, 0.2 mmol) and DIEA (17 µL) in DMF (0.5 mL) was added. The reaction mixture was stirred at room temperature for overnight and was purified using prep-HPLC to give the desired product (14 mg). LC-MS: 428.27 [M+H].

Following compounds were prepared using the procedure described above.

| Compd # | Structure | Chemical Name | TdF Kd (nM) | cERK2 IC50 (nM) | aERK2 IC50 (nM) | Calc. Mass | Obs. M+H | Retention time 10 min method (min.) |
|---|---|---|---|---|---|---|---|---|
| 75 | 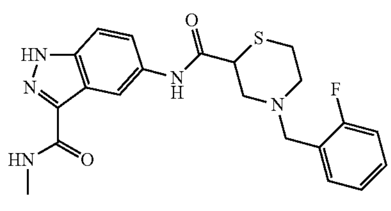 [SMILES: CNC(=O)c1n[nH]c2ccc(NC(=O)C3CN(Cc4ccccc4F)CCS3)cc12] | 5-[[[4-[(2-FLUOROPHENYL)METHYL]-2-THIOMORPHOLINYL]CARBONYL]AMINO]-N-METHYL-1H-INDAZOLE-3-CARBOXAMIDE | 250 | 350.2 | | 427.1 | 428.27 | 2.5 |
| 76 | 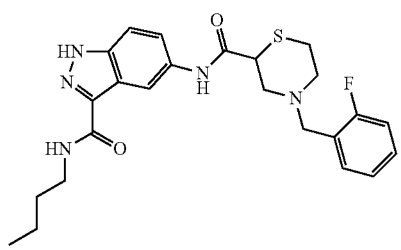 [SMILES: CCCCNC(=O)c1n[nH]c2ccc(NC(=O)C3CN(Cc4ccccc4F)CCS3)cc12] | N-BUTYL-5-[[[4-[(2-FLUOROPHENYL)METHYL]-2-THIOMORPHOLINYL]CARBONYL]AMINO]-1H-INDAZOLE-3-CARBOXAMIDE | 920 | 873.3 | | 469.2 | 470.27 | 3.42 |
| 77 | 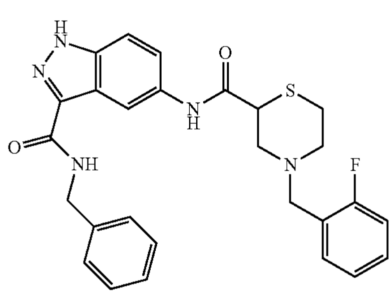 [SMILES: O=C(NCc1ccccc1)c1n[nH]c2ccc(NC(=O)C3CN(Cc4ccccc4F)CCS3)cc12] | 5-[[[4-[(2-FLUOROPHENYL)METHYL]-2-THIOMORPHOLINYL]CARBONYL]AMINO]-N-(PHENYLMETHYL)-1H-INDAZOLE-3-CARBOXAMIDE | 1800 | 3098.7 | | 503.2 | 504.28 | 3.55 |

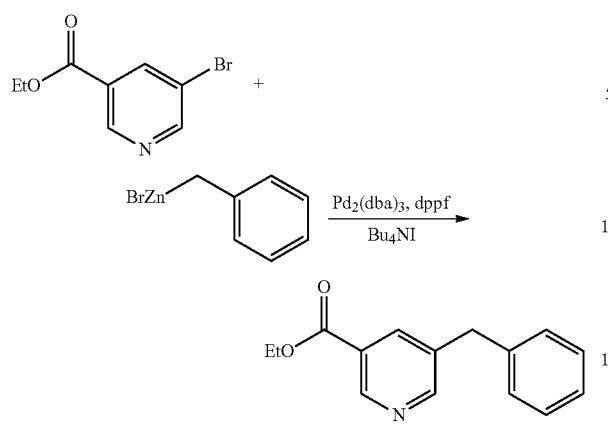

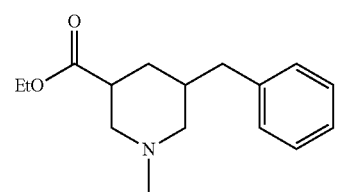

In a flask, acetic acid (5 mL) was added to ethyl 5-benzylpiperidine-3-carboxylate (244 mg) and 1,3,5-trioxane (84 mg). The reaction was stirred for 60 minutes. NaBH3CN (400 mg) was added in one portion. The reaction was stirred for 3 h. The reaction was concentrated in vacuo and purified using prep LC/MS.

Benzylzinc(II) bromide (7 mmol) was added to a vial containing ethyl 5-bromonicotinate (4.35 mmol), Pd2(dba)3 (0.435 mmol), dppf (0.435 mmol) and Bu4NI (13.05 mmol) in 10 mL THF/NMP (1:1). After purging the vial with nitrogen gas, the reaction mixture was stirred and was heated to 70° C. for 4 h. Upon completion, the mixture was quenched by water (30 mL). The mixture was extracted using dichloromethane (3×100 mL). The extracts were combined and dried using anhydrous sodium sulfate. The crude product was purified using flash chromatography.

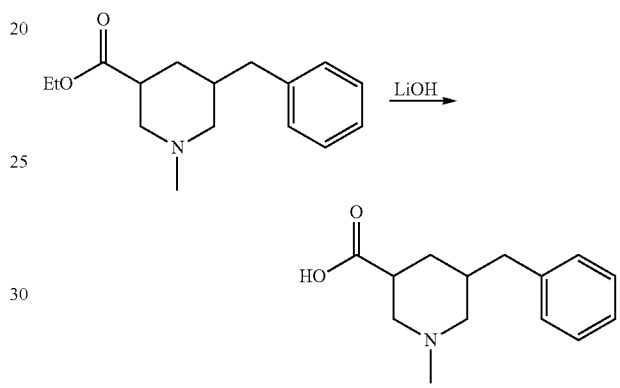

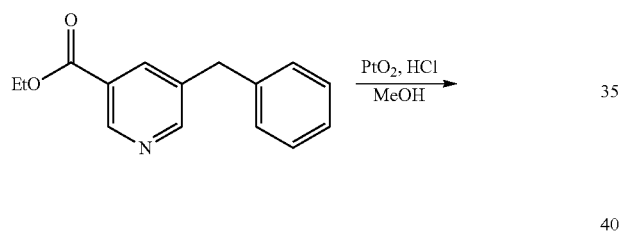

To ethyl 5-benzyl-1-methylpiperidine-3-carboxylate (150 mg), LiOH (3 mmol) was added. The reaction was stirred overnight. The solvent was removed under vacuo. The crude product was progressed to the next step without further purification.

5-benzyl-1-methyl-N-(3-(pyridin-4-yl)-1-trityl-1H-indazol-5-yl)piperidine-3-carboxamide

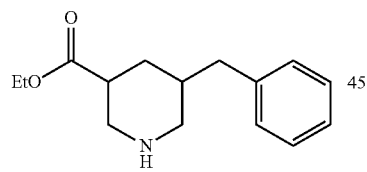

To ethyl 5-benzylnicotinate (250 mg), PtO2 (10 mg) was added. The reaction flask was put under vacuum, and 1.25 N HCl in methanol (10 mL) was added. The reaction was put under 40 psi hydrogen gas and shaked overnight. The reaction mixture was filtered through celite and concentrated under vacuo. The crude product was progressed to the next step without further purification.

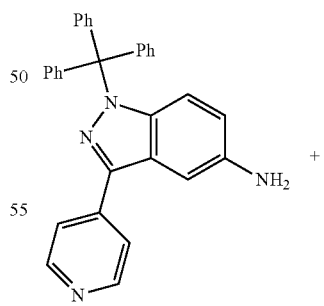

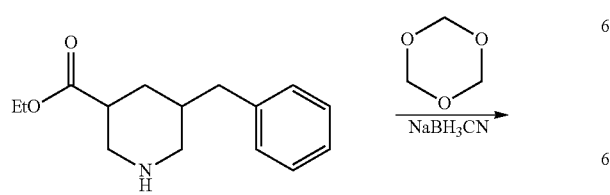

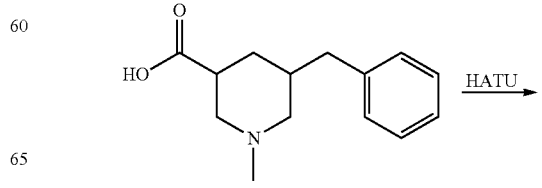

87
-continued

88
5-benzyl-1-methyl-N-(3-(pyridin-4-yl)-1H-indazol-5-yl)piperidine-3-carboxamide

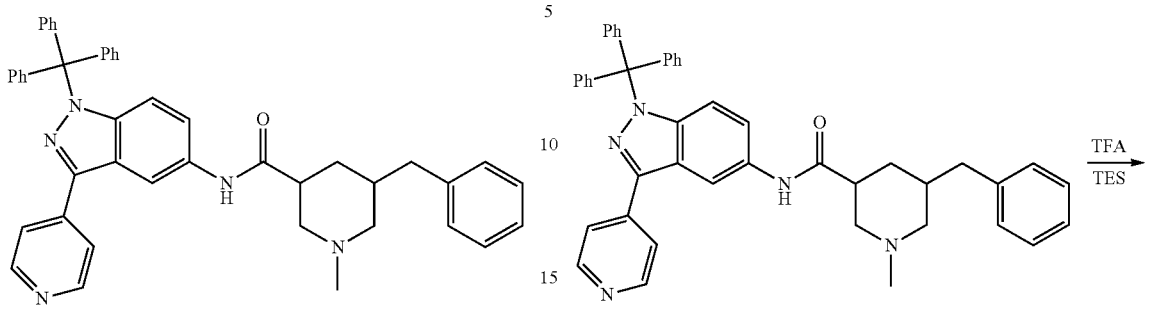

2-(7-Aza-1H-benzotriazole-1-yl)-1,1,3,3-tetramethyluronium hexafluorophosphate (HATU) (0.11 mmol) was added to a suspension of 5-benzyl-1-methylpiperidine-3-carboxylic acid (0.1 mmol) in DMF (0.5 mL) and was stirred at room temperature for 15 minutes. A solution of 3-(pyridin-4-yl)-1-trityl-1H-indazol-5-amine (0.1 mmol) in DMF (0.5 mL) was added to the reaction and followed by diisopropyl ethyl amine (DIEA) (0.1 mL). The mixture was stirred at room temperature for an additional 30 minutes. The reaction was quenched with water (5 mL) and extracted with ethyl acetate (3×10 mL). The extracts were combined, dried using anhydrous sodium sulfate, filtered, and concentrated in vacuo. The crude product was progressed to the next step without purification.

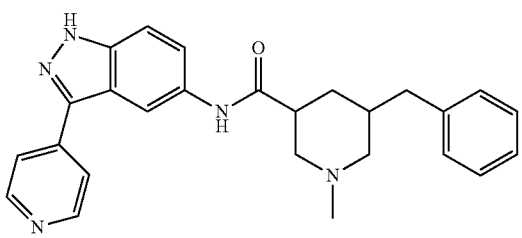

To the product from previous step was added TFA (2 mL) followed by triethylsilane (79 μL, 5 eq.). After stirring at room temperature for 1 hour, the reaction mixture was concentrated on a vacuum and the residue was purified by a prep HPLC to give the desired product.

| Compd # | Structure | aERK2 IC50 (nM) | Calc. Mass | Obs. M + H | Retention time 10 min method (min.) |
|---|---|---|---|---|---|
| 78 | 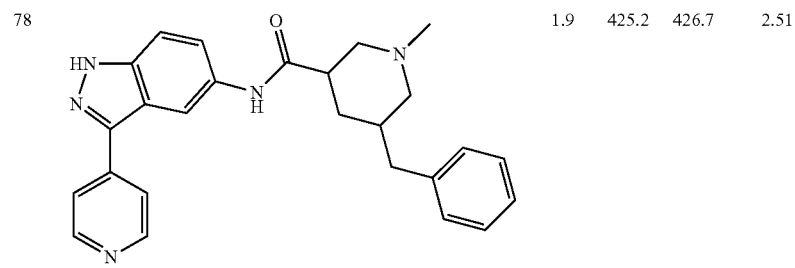 | 1.9 | 425.2 | 426.7 | 2.51 |

Chemical Name
1-METHYL-5-(PHENYLMETHYL)-N-[3-(4-PYRIDINYL)-1H-INDAZOL-5-YL]-3-PIPERIDINECARBOXAMIDE

Synthesis of tert-butyl 3-phenyl-5-(3-(pyridin-4-yl)-1-trityl-1H-indazol-5-ylcarbamoyl)piperidine-1-carboxylate

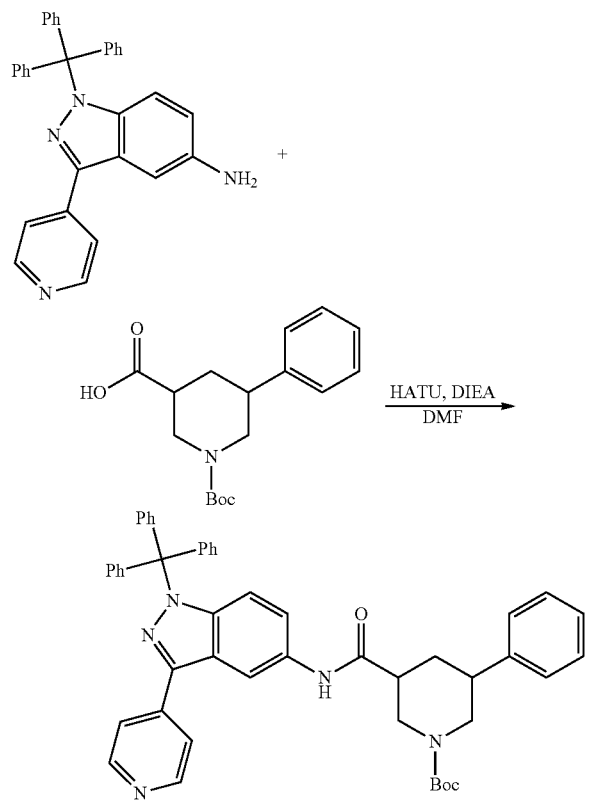

2-(7-Aza-1H-benzotriazole-1-yl)-1,1,3,3-tetramethyluronium hexafluorophosphate (HATU) (49 mg, 0.129 mmol) was added to a suspension of 1-(tert-butoxycarbonyl)-5-phenylpiperidine-3-carboxylic acid (36 mg, 0.117 mmol) in DMF (0.5 mL) and was stirred at room temperature for 15 minutes. A solution of 3-(pyridin-4-yl)-1-trityl-1H-indazol-5-amine (0.117 mmol) in DMF (0 5 mL) was added to the reaction and followed by diisopropyl ethyl amine (DIEA) (0.1 mL). The mixture was stirred at room temperature for an additional 30 minutes. The reaction was quenched with water (5 mL) and extracted with ethyl acetate (3×10 mL). The extracts were combined, dried using anhydrous sodium sulfate, filtered, and concentrated in vacuo. The crude product was progressed to the next step without purification.

Synthesis of 5-phenyl-N-(3-(pyridin-4-yl)-1H-indazol-5-yl)piperidine-3-carboxamide

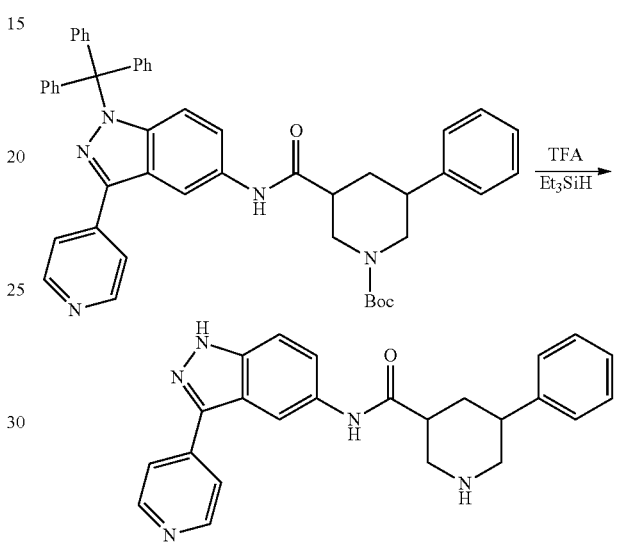

Trifluoroacetic acid (1 mL) was added to tert-butyl 3-phenyl-5-(3-(pyridin-4-yl)-1-trityl-1H-indazol-5-ylcarbamoyl)piperidine-1-carboxylate (0.117 mmol). The reaction was stirred at room temperature for 30 minutes. Triethylsilane (1 drop) was added to the reaction and stirred for an additional 5 minutes. The reaction was concentrated in vacuo and purified using prep LC/MS.

| Compd # | Structure | TdF Kd (nM) | (1) cERK2 IC50 (nM) (2) aERK2 IC50 (nM) | (1) Calc. Mass (2) Obs. M + H | Retention time 10 min method (min.) |
|---|---|---|---|---|---|
| 79 | 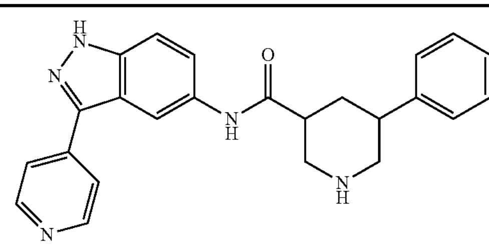 | 8 | (1) 69.4 (2) 123.7 | (1) 397.2 (2) 398.2 | 4.68 |

Chemical Name
5-PHENYL-N-[3-(4-PYRIDINYL)-1H-INDAZOL-5-YL]-3-PIPERIDINECARBOXAMIDE Assays:
TdF Assay for ERK The SAR (Structure Activity Relationship) for ERK ligands covered by this invention was interrogated using the TdF (Temperature Dependence Fluorescence) assay or best known as thermal shift assay [1]. The TdF assay was mainly conducted in the 96-well based CHROMO-4 real time fluorescence plate reader (BioRad). The Sypro Orange (Sigma-Aldrich), environmentally sensitive fluorescence dye, was used to monitor the protein folding-unfolding transition. Protein-ligand binding was gauged by the change (or shift) in the unfolding transition temperature ($\Delta T_m$) acquired at protein alone with respect to protein in the presence of ligand of interest.

Compound of interest was first prepared in DMSO stock (typical concentration: 10 mM). Sample of 20 μL was then added into the 96-well PCR plate, where it consisted of 3 μM. ERK protein and 15, 50 or 100 μM compound (depending on compound's solubility) in buffer (25 mM HEPES, 150 mM NaCl, pH=7.5 and 1mM DTT) incorporated with Sypro Orange dye (5× final concentration). Final percentage of DMSO resided in the sample was 2%. The sample plate was heated from 30° C. to 90° C. with thermal ramping rate of 1° C./min. The fluorescence signals were acquired with excitation and emission wavelengths centered at 490 and 560 nm respectively. The instrument thermal stability was ±0.2° C. The melting temperatures ($T_m$) for ERK protein under aforementioned conditions occurred at 61.0±0.2° C. and 64.8±0.2° C. respectively.

Theoretical Basis for TdF-based Ligand Binding Affinity Constant

The derivation of TdF-based ligand binding affinity constant ($K_d$) followed closely those previously formulated by Brandts and Lin [2]. In brief, the binding constant of the ligand at the $T_m$ is expressed as below:

$$K_L(T_m) = \frac{\{\exp\{-(\Delta H_u(T_0)/R)(1/T_m - 1/T_0) + (\Delta Cp_u/R)[\ln(T_m/T_0) + (T_0/T_m) - 1]\} - 1\}}{[L_{T_m}]}$$

where $T_0$ is the midpoint of unfolding for unliganded protein and $T_m$ is the midpoint of unfolding in presence of ligand. $[L_{T_m}]$ is free ligand at $T_m$. The $\Delta H_u$ and $\Delta Cp_u$ are the enthalpy of unfolding and heat capacity change of unfolding for the protein respectively. Following algorithm derived by Winsor and coworker [3], the $T_0$, $\Delta H_u$ and $\Delta Cp_u$ can be determined separately from nonlinear regression fitting the protein alone melting curve:

$$F(T) = \frac{(Y_n + m_n(T)) + (Y_u + m_u(T))\exp\left\{-\left(\frac{\Delta H_u}{RT}\right)\left(1 - \frac{T}{T_0}\right) + \left(\frac{\Delta Cp_u}{RT}\right)\left(T\ln\left(\frac{T}{T_0}\right) + T_0 - T\right)\right\}}{1 + \exp\left\{-\left(\frac{\Delta H_u}{RT}\right)\left(1 - \frac{T}{T_0}\right) + \left(\frac{\Delta Cp_u}{RT}\right)\left(T\ln\left(\frac{T}{T_0}\right) + T_0 - T\right)\right\}}$$

Where F(T) is the observed fluorescence intensity at any temperature T, $Y_n$ and $Y_u$ are the predicted fluorescence intensities for fully folded and unfolded protein, respectively; $m_n$ and $m_u$ are slope correction for changes in $Y_n$ and $Y_u$ with respect to changes in temperature (analogously replace $T_0$ with $T_m$ in the above equation for liganded protein to yield $T_m$).

Finally, the ligand binding affinity constant at any temperature T (i.e. 25° C.) can be thermodynamically connected to the preceding $K_L(T_m)$ via [2,3]

$$K_L(T) = K_L(T_m)\exp\left\{\left(\frac{-\Delta H_L(T)}{R}\right)\left(\frac{1}{T} - \frac{1}{T_m}\right) + \left(\frac{\Delta Cp_L}{R}\right)\left[\ln\frac{T}{T_m} + 1 - \frac{T}{T_m}\right]\right\}$$

where $\Delta H_L(T)$ is the van't Hoff enthalpy of ligand binding at temperature T and $\Delta Cp_L$ is the heat capacity upon ligand binding. For simplicity, the $\Delta Cp_L$ and $\Delta H_L(T)$ were set to zero and −7 kcal/mol respectively. The uncertainty in the calculated ligand binding affinity constant was estimated to be ±50%.

REFERENCES

1. M. W. Pantoliana, E. C. Petrella, J. D. Kwasnoski, V. S. Lobanov, J. Myslik, E. Graf, T. Carver, E. Asel, B. A. Springer, P. Lane, F. R. Salemme, High-density miniaturized thermal shift assays as a general strategy for drug discovery, *J. Biomol. Screen* 6 (2001) 429-440
2. J. F. Brandts, L.-N. Lin, Study of strong to ultratight protein interactions using differential scanning calorimetry, *Biochemistry* 29 (1990) 6927-6940
3. Mayhood, T. W., Windsor, W. T., Ligand binding affinity determined by temperature-dependent circular dichroism: Cyclin-dependent kinase 2 inhibitors, *Analytical Biochemistry* 345 (2005) 187-197

Coupled ERK2 (cERK) Assay:

Activity of compounds against inactive ERK2 was tested in a coupled MEK1/ERK2 IMAP assay as follows: Compounds were diluted to 25× final test concentration in 100% DMSO. 14 μl of kinase buffer (10 mM Tris.HCl pH 7.2, 10 mM MgCl2, 0.01% Tween-20, 1 mM DTT) containing 0.4 ng unphosphorylated Mouse ERK2 protein was added to each well of a black 384-well assay plate. 1 μl of 25× compound was added to each well and incubated at room temperature for 30 minutes to allow an opportunity for the compound to bind to the inactive enzyme. DMSO concentration during initial incubation is 6.7%. ERK2 activity was determined to be insensitive to DMSO concentrations up to 20%. ERK2 was then activated and it's kinase activity measured by the addition of 10 μl kinase buffer with the following components (final concentration per reaction): 2 ng active (phosphorylated) human MEK1 protein and 4 μM (total) ERK2 IMAP substrate peptides (3.9 μM unlabeled IPTTPITTTYFFFK-CONH2 and 100 nM IPTTPITTTYFFFK(5-carboxyfluorescein)-CONH2) and 30 μM ATP. DMSO concentration during ERK activation was 4%. After one hour, reactions were terminated by addition of 60 μl IMAP detections beads in binding buffer (Molecular Devices). Binding was allowed to equilibrate for 30 minutes before reading the plate on an LJL Analyst Fluorescence Polarization plate reader. Compound inhibition was calculated relative to DMSO and fully inhibited standards. Active compounds were reconfirmed in an independent assay.

Active ERK2 (aERK) Assay:

Activated ERK2 activity was also determined in the IMAP assay format using the procedure outlined above. 1 μl of 25× compound was added to 14 μl of kinase buffer containing 0.25 ng fully phosphorylated, active Mouse ERK2 protein. Following a 30 minute incubation, the reactions were initiated by addition of 10 μl of kinase buffer containing 1 μM ERK2 IMAP substrate peptide (0.9 μM unlabeled IPTTPITTTY-FFFK--CONH2 and 100 nM IPTTPITTTYFFFK(5-carboxyfluorescein)-CONH2) and 30 μM ATP. Reactions proceeded for 30 minutes before termination by addition of 60 μl IMAP detection beads in binding buffer. Plates were read as above after 30 minute binding equilibration. Active compounds were reconfirmed in an independent assay.

Values for Kd TdF (nM), cERK IC50 (nM) and aERK. IC50 (nM) for individual compounds have been set forth above in above Tables. In one embodiment, the compounds of the present invention have aERK IC50 values of from about 0.05 nM to 1 μM; and in a preferred embodiment, less than 100 nM (<100 nM); and in a more preferred embodiment less than 10 nM (<10 nM).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

Each and every reference publication referred to hereinabove is incorporated herein by reference in its entirety for all purposes.

What is claimed is:

1. A compound of Formula I

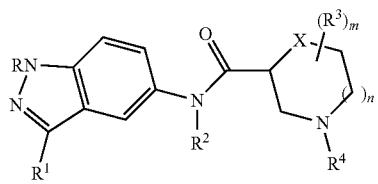

(I)

or a pharmaceutically acceptable salt thereof, wherein:
R is H;
$R^1$ is selected from the group consisting of aryl, heterocyclyl and —C(=O)—$NR^5R^6$;
$R^2$ is H or alkyl;
X is selected from the group consisting of —O—;
each $R^3$ independently is selected from the group consisting of alkyl, aryl, hydroxyl, and —S-alkyl, or wherein two $R^3$ groups together with the same carbon atom to which both are attached form =O;
m is 0, 1, or 2;
n is 0 or 1;
$R^4$ is selected from the group consisting of H, alkyl, aryl, —C(=O)-aryl, and —C(=O)—O-alkyl;
$R^5$, $R^6$, and $R^7$ independently are H or alkyl;
$R^8$ and $R^9$ independently are H, alkyl or aryl; or $R^8$ and $R^9$ with the carbon atom to which they are attached form a heterocyclyl ring.

2. The compound of claim 1 wherein $R^1$ is heterocyclyl which is pyridyl.

3. The compound of claim 1, wherein $R^1$ is —C(=O)—$NR^5R^6$ wherein $R^5$ is H and $R^6$ is alkyl.

4. The compound of claim 3, wherein said $R^6$ alkyl is unsubstituted or substituted with an aryl substituent.

5. The compound of claim 1, wherein $R^2$ is H.

6. The compound of claim 1, wherein m is 0.

7. The compound of claim 1, wherein m is 1, and $R^3$ is selected from the group consisting of alkyl, aryl, hydroxyl, and —S-alkyl; wherein said $R^3$ alkyl is hydroxymethyl and said $R^3$ aryl is phenyl.

8. The compound of claim 1, wherein m is 2, and the two $R^3$ groups together with the carbon atom to which both are attached form —C(=O)—.

9. The compound of claim 1, wherein

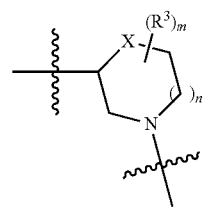

is

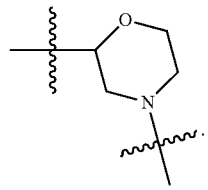

10. The compound of claim 1, wherein $R^4$ is alkyl, which is unsubstituted or substituted with at least one substitutent selected from the group consisting of aryl and heteroaryl.

11. The compound of claim 10, wherein said $R^4$ is alkyl which is substituted with a heteroaryl selected from the group consisting of pyridyl, thiazolyl, and thiophenyl.

12. The compound of claim 1, selected from the group consisting of:

N-[3-[6-(1-METHYLETHOXY)-3-PYRIDINYL]-1H-INDAZOL-5-YL]-4-(PHENYLMETHYL)-2-MORPHOLINECARBOXAMIDE;

N-[3-[6-(1-METHYLETHOXY)-3-PYRIDINYL]-1H-INDAZOL-5-YL]-2-MORPHOLINECARBOXAMIDE;

N-[3-(4-PYRIDINYL)-1H-INDAZOL-5-YL]-4-(4-THIAZOLYLMETHYL)-2-MORPHOLINECARBOXAMIDE;

N-[3-(4-PYRIDINYL)-1H-INDAZOL-5-YL]-4-(3-THIENYLMETHYL)-2-MORPHOLINECARBOXAMIDE;

4-[(2-FLUOROPHENYL)METHYL]-N-[3-(4-PYRIDINYL)-1H-INDAZOL-5-YL]-2-MORPHOLINECARBOXAMIDE;

N-[3-(4-PYRIDINYL)-1H-INDAZOL-5-YL]-4-(2-PYRIDINYLMETHYL)-2-MORPHOLINECARBOXAMIDE;

N-[3-(4-PYRIDINYL)-1H-INDAZOL-5-YL]-4-(2-PYRIDINYLMETHYL)-2-MORPHOLINECARBOXAMIDE;

4-[(2-BROMOPHENYL)METHYL]-N-[3-(4-PYRIDINYL)-1H-INDAZOL-5-YL]-2-MORPHOLINECARBOXAMIDE;

4-[(2-CHLOROPHENYL)METHYL]-N-[3-(4-PYRIDINYL)-1H-INDAZOL-5-YL]-2-MORPHOLINECARBOXAMIDE;

N-[3-(4-PYRIDINYL)-1H-INDAZOL-5-YL]-2-MORPHOLINECARBOXAMIDE;

4-[(2-METHYL-4-THIAZOLYL)METHYL]-N-[3-(4-PYRIDINYL)-1H-INDAZOL-5-YL]-2-MORPHOLINECARBOXAMIDE;

N-[3-(4-PYRIDINYL)-1H-INDAZOL-5-YL]-4-(3-PYRIDINYLMETHYL)-2-MORPHOLINECARBOXAMIDE;

4-(PHENYLMETHYL)-N-[3-(4-PYRIDINYL)-1H-INDAZOL-5-YL]-2-MORPHOLINECARBOXAMIDE;

4-[(4-CHLOROPHENYL)METHYL]-N-[3-(4-PYRIDINYL)-1H-INDAZOL-5-YL]-2-MORPHOLINECARBOXAMIDE;

4-[(3-METHOXYPHENYL)METHYL]-N-[3-(4-PYRIDINYL)-1H-INDAZOL-5-YL]-2-MORPHOLINECARBOXAMIDE;

4-[(3-CHLOROPHENYL)METHYL]-N-[3-(4-PYRIDINYL)-1H-INDAZOL-5-YL]-2-MORPHOLINECARBOXAMIDE;

4-[(4-CYANOPHENYL)METHYL]-N-[3-(4-PYRIDINYL)-1H-INDAZOL-5-YL]-2-MORPHOLINECARBOXAMIDE;

4-[(3-CYANOPHENYL)METHYL]-N-[3-(4-PYRIDINYL)-1H-INDAZOL-5-YL]-2-MORPHOLINECARBOXAMIDE;

4-[(2-CYANOPHENYL)METHYL]-N-[3-(4-PYRIDINYL)-1H-INDAZOL-5-YL]-2-MORPHOLINECARBOXAMIDE;

4-[(4-METHOXYPHENYL)METHYL]-N-[3-(4-PYRIDINYL)-1H-INDAZOL-5-YL]-2-MORPHOLINECARBOXAMIDE;

4-[[4-(METHYLTHIO)PHENYL]METHYL]-N-[3-(4-PYRIDINYL)-1H-INDAZOL-5-YL]-2-MORPHOLINECARBOXAMIDE;

4[(2-METHOXYPHENYL)METHYL]-N-[3-(4-PYRIDINYL)-1H-INDAZOL-5-YL]-2-MORPHOLINECARBOXAMIDE;

4-[(2-CHLORO-6-FLUOROPHENYL)METHYL]-N-[3-(4-PYRIDINYL)-1H-INDAZOL-5-YL]-2-MORPHOLINECARBOXAMIDE;

4-[(2-FLUORO-4-METHOXYPHENYL)METHYL]-N-[3-(4-PYRIDINYL)-1H-INDAZOL-5-YL]-2-MORPHOLINECARBOXAMIDE;

4-[[2-FLUORO-6-(TRIFLUOROMETHYL)PHENYL]METHYL]-N-[3-(4-PYRIDINYL)-1H-INDAZOL-5-YL]-2-MORPHOLINECARBOXAMIDE;

4-[(2-FLUORO-4,5-DIMETHOXYPHENYL)METHYL]-N-[3-(4-PYRIDINYL)-1H-INDAZOL-5-YL]-2-MORPHOLINECARBOXAMIDE;

4-[(4-CHLORO-2-FLUOROPHENYL)METHYL]-N-[3-(4-PYRIDINYL)-1H-INDAZOL-5-YL]-2-MORPHOLINECARBOXAMIDE;

4-[[2-FLUORO-3-(TRIFLUOROMETHYL)PHENYL]METHYL]-N-[3-(4-PYRIDINYL)-1H-INDAZOL-5-YL]-2-MORPHOLINECARBOXAMIDE;

4-[[2-FLUORO-5-(TRIFLUOROMETHYL)PHENYL]METHYL]-N-[3-(4-PYRIDINYL)-1H-INDAZOL-5-YL]-2-MORPHOLINECARBOXAMIDE;

4-[(2,3-DIFLUOROPHENYL)METHYL]-N-[3-(4-PYRIDINYL)-1H-INDAZOL-5-YL]-2-MORPHOLINECARBOXAMIDE;

4-[(2,6-DIFLUOROPHENYL)METHYL]-N-[3-(4-PYRIDINYL)-1H-INDAZOL-5-YL]-2-MORPHOLINECARBOXAMIDE;

4-[(2,4-DIFLUOROPHENYL)METHYL]-N-[3-(4-PYRIDINYL)-1H-INDAZOL-5-YL]-2-MORPHOLINECARBOXAMIDE;

4-[(2-FLUORO-5-METHOXYPHENYL)METHYL]-N-[3-(4-PYRIDINYL)-1H-INDAZOL-5-YL]-2-MORPHOLINECARBOXAMIDE;

4-[(3-CHLORO-2,6-DIFLUOROPHENYL)METHYL]-N-[3-(4-PYRIDINYL)-1H-INDAZOL-5-YL]-2-MORPHOLINECARBOXAMIDE;

4-[(2-CHLORO-3,6-DIFLUOROPHENYL)METHYL]-N-[3-(4-PYRIDINYL)-1H-INDAZOL-5-YL]-2-MORPHOLINECARBOXAMIDE;

4-[(3-CHLORO-4-FLUOROPHENYL)METHYL]-N-[3-(4-PYRIDINYL)-1H-INDAZOL-5-YL]-2-MORPHOLINECARBOXAMIDE;

4-[(3,5-DICHLOROPHENYL)METHYL]-N-[3-(4-PYRIDINYL)-1H-INDAZOL-5-YL]-2-MORPHOLINECARBOXAMIDE; and 4-[(2,5-DIFLUOROPHENYL)METHYL]-N-[3-(4-PYRIDINYL)-1H-INDAZOL-5-YL]-2-MORPHOLINECARBOXAMIDE;

or a pharmaceutically acceptable salt thereof.

13. A pharmaceutical composition comprising at least one compound of claim 1, or a pharmaceutically acceptable salt thereof, and a pharmaceutically acceptable carrier.

* * * * *